US008808204B2

United States Patent
Irisawa et al.

(10) Patent No.: US 8,808,204 B2
(45) Date of Patent: Aug. 19, 2014

(54) HIGH-FREQUENCY OPERATION APPARATUS AND OPERATION APPARATUS

(75) Inventors: Takashi Irisawa, Hachioji (JP); Sadayoshi Takami, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/571,537

(22) Filed: Aug. 10, 2012

(65) Prior Publication Data

US 2013/0066238 A1    Mar. 14, 2013

Related U.S. Application Data

(63) Continuation of application No. PCT/JP2012/052076, filed on Jan. 31, 2012.

(60) Provisional application No. 61/441,323, filed on Feb. 10, 2011.

(51) Int. Cl.
| | | |
|---|---|---|
| A61H 1/00 | (2006.01) | |
| A61N 7/00 | (2006.01) | |
| A61H 23/02 | (2006.01) | |
| A61N 7/02 | (2006.01) | |

(52) U.S. Cl.
CPC .............. *A61N 7/00* (2013.01); *A61H 23/0245* (2013.01); *A61N 7/02* (2013.01)
USPC .......................................................... 601/2

(58) Field of Classification Search
CPC ........ A61N 7/00; A61N 7/02; A61H 23/0245
USPC .......................................................... 601/2
See application file for complete search history.

(56) References Cited

U.S. PATENT DOCUMENTS

2002/0032439 A1    3/2002    Hareyama

FOREIGN PATENT DOCUMENTS

| EP | 1810630 | * | 7/2007 |
|---|---|---|---|
| JP | 10-286261 | | 10/1998 |
| JP | 2000-201944 | | 7/2000 |
| JP | 2003-284725 | | 10/2003 |
| JP | 2009-160404 | | 7/2009 |
| JP | 4567812 | | 8/2010 |
| WO | WO 2010/044354 A1 | | 4/2010 |

\* cited by examiner

*Primary Examiner* — Tse Chen
*Assistant Examiner* — Hien Nguyen
(74) *Attorney, Agent, or Firm* — Scully, Scott, Murphy & Presser, P.C.

(57) ABSTRACT

A high-frequency operation apparatus includes a grasping portion for grasping a treatment target living tissue, an electrode for supplying a high-frequency current to the living tissue, a high-frequency current supplying section that generates the high-frequency current necessary for treatment, a cable section that transmits the high-frequency current, an impedance measuring section for measuring an impedance value of the living tissue, a detecting section that detects that the impedance value reaches an impedance threshold at a time when moisture in the living tissue starts to evaporate, a measuring section that measures an output time of the high-frequency current after the detection, a storing section that stores a set time, and an output control section that performs control for stopping an output when the output time of the high-frequency current reaches the stored set time.

8 Claims, 14 Drawing Sheets

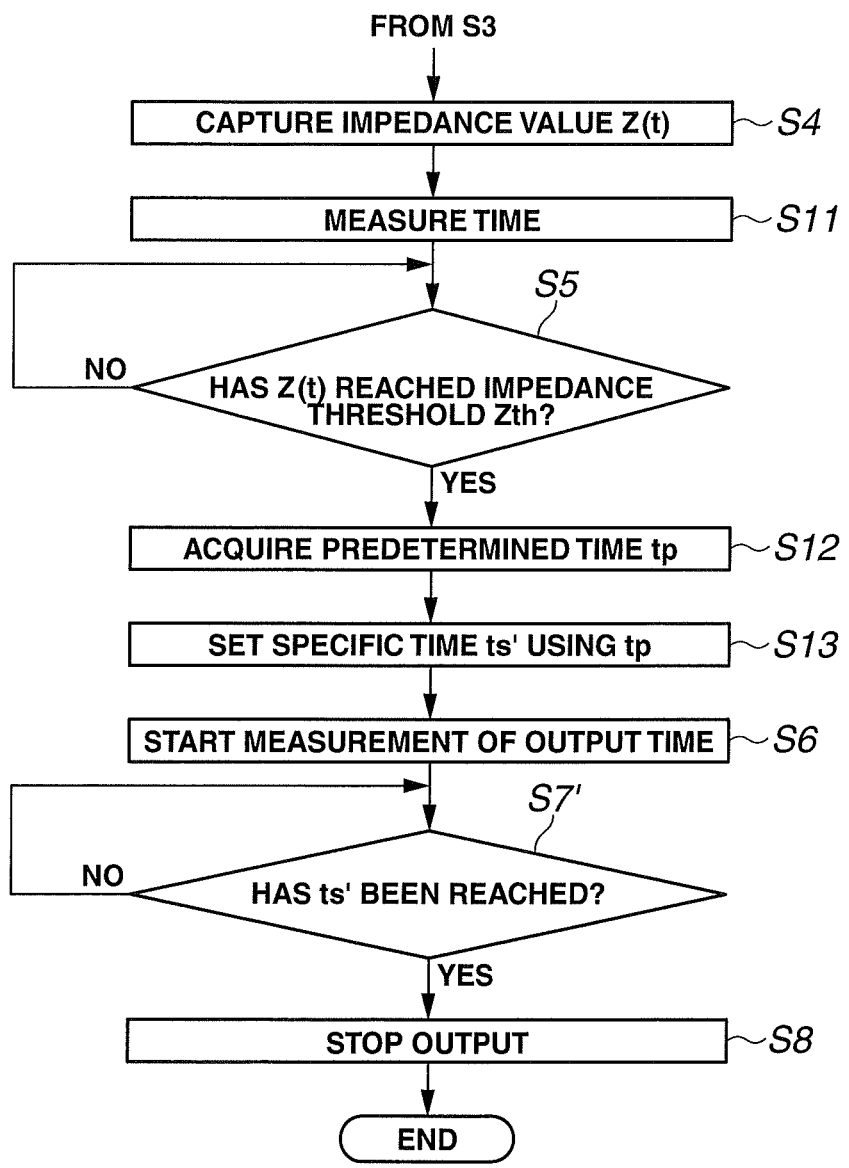

US 8,808,204 B2

HIGH-FREQUENCY OPERATION APPARATUS AND OPERATION APPARATUS

CROSS REFERENCE TO RELATED APPLICATION

This application is a continuation application of PCT/JP2012/052076 filed on Jan. 31, 2012 and claims benefit of U.S. Provisional Patent Application No. 61/441,323 filed in the U.S.A. on Feb. 10, 2011, the entire contents of which are incorporated herein by this reference.

BACKGROUND OF THE INVENTION

1. Field of the Invention

The present invention relates to a high-frequency operation apparatus and an operation apparatus for supplying a high-frequency current or the like to a living tissue and performing an operation.

2. Description of the Related Art

In recent years, various operation apparatuses are used in a surgical operation and the like. For example, a technique for administering high-frequency energy to a blood vessel and performing treatment has been known conventionally. In the case of this technique, a high-frequency operation apparatus is used that feeds a high-frequency current in a state in which the blood vessel is grasped with an appropriate grasping force and seals the blood vessel with thermal energy generated when the high-frequency current is fed.

For example, an electrical surgical operation apparatus disclosed in Japanese Patent Application Laid-Open Publication No. 10-286261 measures electrical impedance of a living tissue while supplying a high-frequency current to the living tissue and stops an output and ends treatment when the electrical impedance reaches a threshold or after a fixed time.

SUMMARY OF THE INVENTION

A high-frequency operation apparatus according to an aspect of the present invention includes: a grasping portion for grasping a treatment target living tissue; an electrode provided in the grasping portion and for supplying a high-frequency current to the living tissue; a high-frequency current supplying section that generates the high-frequency current necessary for treatment of the living tissue via the electrode; a high-frequency current transmitting member that transmits the high-frequency current generated by the high-frequency current supplying section to the electrode; an impedance measuring section for measuring an impedance value of the living tissue; a detecting section that detects whether the impedance value measured by the impedance measuring section reaches an impedance threshold at a time when moisture in the living tissue starts to evaporate; a time measuring section that measures an output time of the high-frequency current at least after the detecting section detects that the impedance value of the living tissue reaches the impedance threshold; a storing section that stores a set time set based on a length of the high-frequency current transmitting member and an area of the electrode; and an output control section that determines whether the output time of the high-frequency current measured by the time measuring section reaches the set time stored in the storing section and transmits, when it is determined that the output time reaches the set time, an output stop signal for the high-frequency current to the high-frequency current supplying section.

An operation apparatus according to another aspect of the present invention includes: a grasping portion for grasping a treatment target living tissue; a treatment member provided in the grasping portion and for applying treatment to the living tissue using ultrasound vibration; an ultrasound vibration supplying section for supplying the ultrasound vibration to the living tissue via the treatment member; an electrode provided in the treatment member and for applying treatment to the living tissue using a high-frequency current; a high-frequency current supplying section for supplying the high-frequency current to the living tissue via the electrode; a high-frequency current transmitting member that transmits the high-frequency current supplied from the high-frequency current supplying section to the electrode; an impedance measuring section for measuring an impedance value of the living tissue; a detecting section that detects whether the impedance value measured by the impedance measuring section reaches an impedance threshold at a time when moisture in the living tissue starts to evaporate; a time measuring section that measures an output time of the high-frequency current and the ultrasound vibration at least after the detecting section detects that the impedance value of the living tissue reaches the impedance threshold; a storing section that stores a set time set based on a length of the high-frequency current transmitting member and an area of the electrode; and an output control section that determines whether the output time of the high-frequency current and the ultrasound vibration measured by the time measuring section reaches the set time stored in the storing section and performs, when it is determined that the output time reaches the set time, control for stopping an output of the ultrasound vibration by the ultrasound vibration supplying section and the high-frequency current by the high-frequency current supplying section.

BRIEF DESCRIPTION OF THE DRAWINGS

FIG. 7B is a flowchart for explaining a part of a processing procedure in the modification;

DETAILED DESCRIPTION OF THE PREFERRED EMBODIMENTS

Embodiments of the present invention are explained below with reference to the drawings.

First Embodiment

Figure 1:
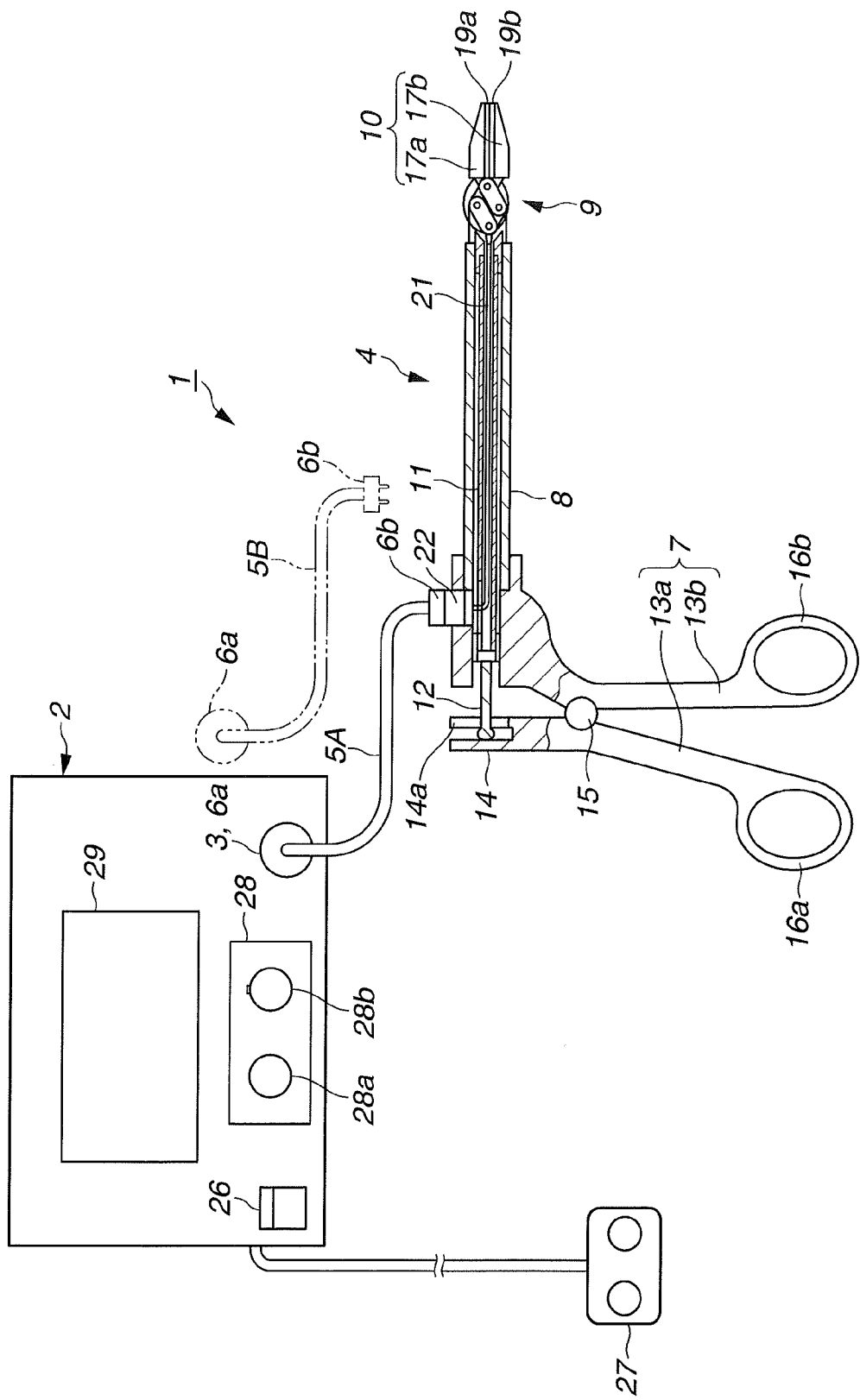
FIG. 1 is a diagram showing an overall configuration of a high-frequency operation apparatus according to a first embodiment of the present invention.

As shown in FIG. 1, a high-frequency operation apparatus 1 according to a first embodiment of the present invention includes a high-frequency power supply device 2 functioning as a high-frequency current supplying section for supplying a high-frequency current to a treatment target living tissue.

In the high-frequency power supply device 2, a connector bearing 3 for outputting the high-frequency current is provided. A connector 6a provided at a proximal end of a cable section 5A for connecting a high-frequency probe (hereinafter abbreviated as probe) 4 included in a high-frequency treatment instrument is detachably connected to the connector bearing 3. The probe 4 can also be used by using a cable section 5B indicated by an alternate long and two short dashes line having length different from length of the cable section 5A instead of the cable section 5A.

Instead of the probe 4, a probe having different sheath length of a sheath 8 of the probe 4 can also be used. A high-frequency treatment instrument obtained by integrating the probe 4 and the cable sections 5A and 5B can also be used while being connected to the high-frequency power supply device 2.

The probe 4 includes an operation section 7 that a surgeon grasps to perform operation, the sheath 8 extended from an upper end side of the operation section 7, and a treatment section 10 that is provided via a link mechanism 9 at a distal end of the sheath 8 and feeds a high-frequency current to a treatment target living tissue and performs treatment of sealing or coagulation.

A slide pipe 11 is inserted through the sheath 8. A rear end of the slide pipe 11 is coupled to a connecting shaft bearing 14 at an upper end of one of handles 13a and 13b, which form the operation section 7, via a connecting shaft 12. A slit 14a that allows a rear end side of the connecting shaft 12 to pass and does not allow a spherical portion of the rear end to pass is provided in the connecting shaft bearing 14.

The handles 13a and 13b are pivotably coupled in a pivoted section 15. Finger holding sections 16a and 16b are provided on a lower end side.

The surgeon performs operation for opening and closing the finger holding sections 16a and 16b, whereby upper end sides of the handles 13a and 13b move in opposite directions. By performing the operation, the surgeon can push out the slide pipe 11 to a front and move the slide pipe 11 to a rear.

A distal end of the slide pipe 11 is coupled to a pair of treatment members 17a and 17b included in the treatment section 10 via a link mechanism 9 for opening and closing the treatment members 17a and 17b.

Therefore, the surgeon can drive, by performing operation for opening and closing the handles 13a and 13b, the link mechanism 9 coupled to the slide pipe 11, which moves back and forth, and open and close the pair of treatment members 17a and 17b. The opening and closing pair of treatment members 17a and 17b form a grasping portion for grasping, for example, a blood vessel 18 (see FIG. 2) as a treatment target living tissue using two inner surface portions opposed to each other on an inner side of the treatment members 17a and 17b.

A state shown in FIG. 1 is a state in which the handles 13a and 13b are closed. When the operation for opening the handles 13a and 13b is performed from this state, the slide pipe 11 moves forward. The pair of treatment members 17a and 17b can be opened via the link mechanism 9.

Bipolar electrodes 19a and 19b are provided in opposed inner surface portions in the pair of treatment members 17a and 17b formed of an insulating member. Rear end sides of the treatment members 17a and 17b are coupled to the link mechanism 9.

A pair of cables 21 are inserted through the slide pipe 11 and are respectively connected to the electrodes 19a and 19b. Rear ends of the cables 21 are connected to a connector bearing 22 provided, for example, at an upper end of the handle 13b. A connector 6b at the other end of the cable section 5A is detachably connected to the connector bearing 22.

A foot switch 27 functioning as an output switch for performing instruction operation for output ON (energization) and output OFF (interruption) of a high-frequency current is connected to the high-frequency power supply device 2 besides a power switch 26. The surgeon can supply the high-frequency current to the treatment section 10 side and stop the supply by performing operation for stepping on the foot switch 27 with a foot.

A setting section 28 that performs setting of, for example, a value of high-frequency power is provided on a front surface of the high-frequency power supply device 2. The setting section 28 is provided with a setting button 28a for setting a value of high-frequency power and setting an impedance threshold Zth and a specific time (set time) is explained below and an output mode selection switch 28b for performing selection of an output mode from a continuous output mode for continuously outputting the high-frequency current and an intermittent output mode for intermittently outputting the high-frequency current. The surgeon can set a value of high-frequency power suitable for treatment, set an output mode and the like in use, and perform a high-frequency operation.

A display section 29 that displays, for example, a set value of high-frequency power is provided on an upper side of the setting section 28.

Figure 2:
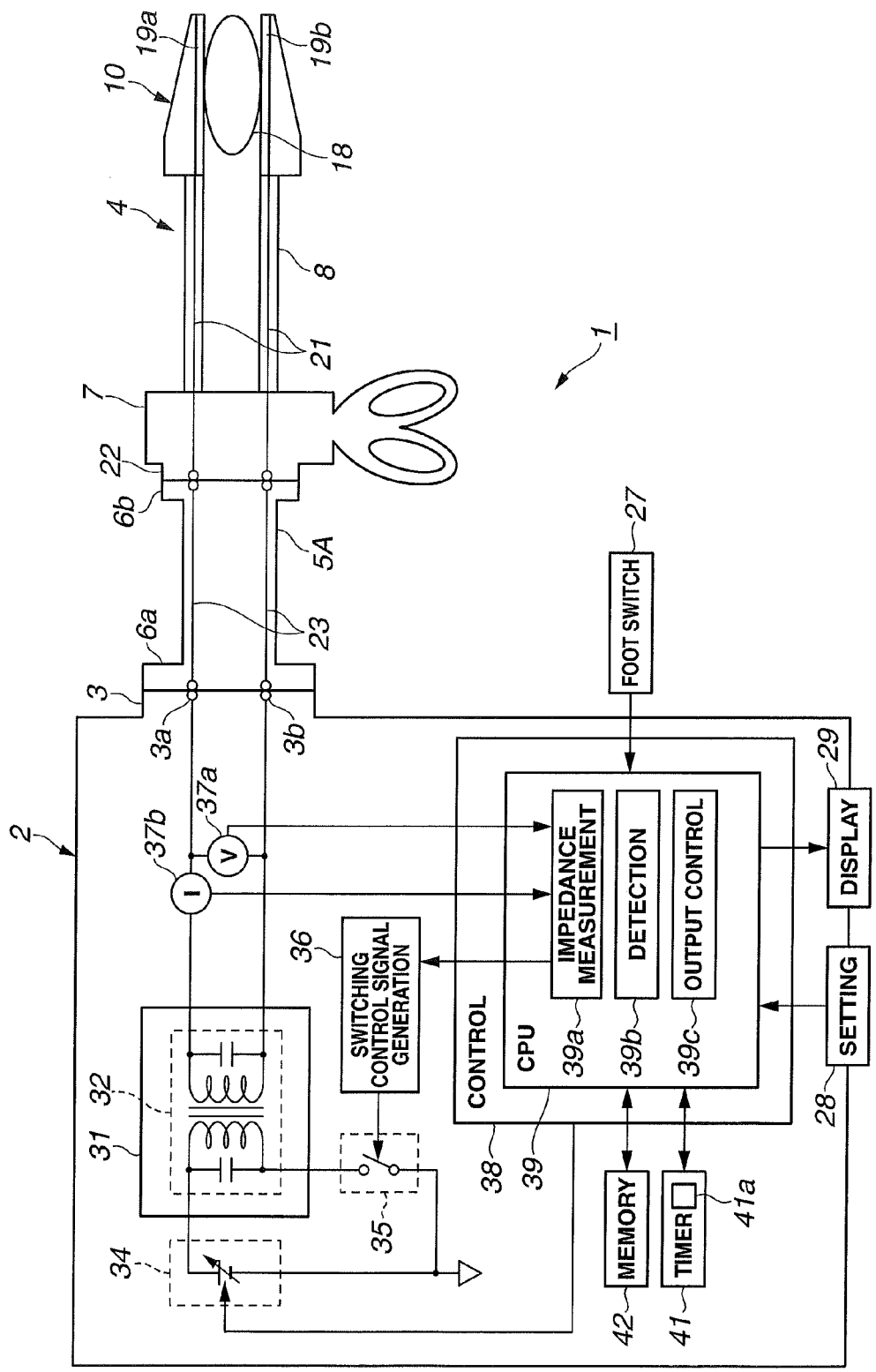
FIG. 2 is a block diagram showing an internal configuration of a high-frequency power supply device in the high-frequency operation apparatus.

As shown in FIG. 2, in the high-frequency power supply device 2, a high-frequency current generating section 31 that generates a high-frequency current is configured using an isolation transformer 32. A parallel resonant circuit in which capacitors are connected in parallel is provided on a primary winding side of the isolation transformer 32. A direct-current voltage is applied to one end of the parallel resonant circuit from a variable power supply 34. A switching circuit 35 is connected to the other end.

The variable power supply 34 can change and output the direct-current voltage. The switching circuit 35 performs switching according to application of a switching control signal from a switching control signal generating section 36.

The switching circuit 35 switches an electric current flowing from the variable power supply 34 to a primary winding of the isolation transformer 32 and generates a boosted high-frequency current in an output section on a secondary winding side of the isolation transformer 32 in a state in which the secondary winding side is insulated from a primary winding side. A capacitor is connected to the secondary winding as well.

The output section on the secondary winding side of the isolation transformer 32 is connected to contacts 3*a* and 3*b* of the connector bearing 3, which is an output end of the high-frequency current. The high-frequency current is transmitted to the probe 4 via a cable 23 in the cable section 5A connected to the connector bearing 3.

The high-frequency current transmitted to the probe 4 is transmitted to the electrodes 19*a* and 19*b* via the cables 21 in the probe 4. The high-frequency current is supplied (applied) to the blood vessel 18 or the like, which is the treatment target living tissue, in contact with the electrodes 19*a* and 19*b* to make it possible to perform treatment of coagulation (sealing).

A high-frequency current transmitting member (a functioning as a cable section) that transmits the high-frequency current from the high-frequency current generating section 31 to the electrodes 19*a* and 19*b* is the cable section 5A and the cables 21 in the probe in the case of FIG. 2. However, in the case of a probe obtained by integrating the cable section 5A with the probe 4, the high-frequency current transmitting member is a cable in the probe.

A voltage sensor 37*a* for measuring a voltage and a current sensor 37*b* for measuring an electric current are provided at both ends of the output section.

A voltage between output ends (the two contacts 3*a* and 3*b*) in a state in which the high-frequency current is fed to the living tissue, for example, the blood vessel 18 as shown in FIG. 2 and an electric current flowing to a load (living tissue) side are measured by the voltage sensor 37*a* and the current sensor 37*b*.

A voltage value and a current value measured respectively by the voltage sensor 37*a* and the current sensor 37*b* are inputted to a CPU 39 included in a control section 38.

The CPU 39 has a function of an impedance measuring section 39*a* that measures (calculates), from the measured voltage value and current value, an electrical impedance value (simply abbreviated as impedance value) $Z(t)$ on the load side including the living tissue by dividing the voltage value by the current value. $Z(t)$ indicates that a value of $Z(t)$ changes according to (elapse of) time t after time when the high-frequency current is supplied (outputted) to the living tissue to start treatment.

A configuration may be adopted in which the impedance measuring section 39*a* is provided on an outside of the control section 38 or the CPU 39 and the measured (calculated) impedance value $Z(t)$ is outputted to the control section 38 or the CPU 39. The impedance measuring section 39*a* may be defined by a configuration including the voltage sensor 37*a* and the current sensor 37*b*.

The CPU 39 has a function of a detecting section (or a determining section) 39*b* that monitors the measured impedance value $Z(t)$ and detects (or determines) whether the impedance value $Z(t)$ reaches the impedance threshold Zth, which is a specific impedance value, set according to characteristics of the living tissue. The impedance threshold Zth is equivalent to a specific impedance value indicated by the living tissue in a state in which moisture in the living tissue starts to evaporate as explained below.

The CPU 39 included in the control section 38 is connected to a timer 41 functioning as a time measuring section 41*a* that performs time measurement, a memory 42 functioning as a storing section that stores various kinds of information such as the impedance threshold Zth and the specific time ts, the foot switch 27 functioning as the output switch for performing output ON and output OFF of the high-frequency current, a setting section 28, and a display section 29.

The CPU 39 included in the control section 38 that performs control of the respective sections of the high-frequency power supply device 2 transmits a control signal for controlling operations of the variable power supply 34 and the switching control signal generating section 36.

The variable power supply 34 outputs a direct-current voltage corresponding to the control signal transmitted from the CPU 39. The switching control signal generating section 36 outputs a switching signal having a waveform (e.g., a rectangular wave) corresponding to the control signal transmitted from the CPU 39.

The high-frequency current generating section 31 generates a high-frequency current according to an operation of the switching circuit 35 turned on and off by direct-current power transmitted from the variable power supply 34 and the rectangular wave transmitted from the switching control signal generating section 36 and outputs the high-frequency current from the connector bearing 3. The parallel resonant circuit of the primary winding of the isolation transformer 32 reduces spurious due to the rectangular wave obtained by performing a switching operation. The output section also forms a resonant circuit and reduces spurious.

The CPU 39 performs control of the respective sections according to a computer program stored in the memory 42 when treatment of coagulation for the living tissue is performed.

The CPU 39 sets the specific time ts, which is stored in the memory 42, in the timer 41 at timing when it is detected by the function of the detecting section 39*b* that the measured impedance value $Z(t)$ reaches the impedance threshold Zth and causes the timer 41 to perform time measurement of the specific time ts. The timer 41 starts, from timing when the impedance value $Z(t)$ reaches the impedance threshold Zth, measurement of an output time in which the high-frequency current is outputted to the living tissue side and outputs a timing signal to the CPU 39 at timing when the output time reaches the specific time ts when the treatment of coagulation is completed.

The CPU 39 may cause the timer 41 to simply measure the output time and may determine whether the output time measured by the timer 41 reaches the specific time ts.

At timing when it is detected that the output time reaches the specific time ts, the CPU 39 sends, for example, a control signal for setting the power supply voltage of the variable power supply 34 to zero. The CPU 39 performs control for setting the power supply voltage of the variable power supply 34 to zero and stopping an output from the high-frequency current generating section 31.

In other words, the CPU 39 has a function of an output control section 39*c* that performs control for stopping supply (stopping output) of the high-frequency current supplied (outputted) from the high-frequency power supply device 2 functioning as the high-frequency current supply section to the living tissue after time elapse of the specific time ts from the timing when the measured impedance value Z(t) reaches the impedance threshold Zth.

When the output control section 39c performs the control for stopping the supply (the output) of the high-frequency current, the control is not limited to the control for setting the power supply voltage of the variable power supply 34 to zero according to the control signal. The control signal only has to be a control signal (referred to as output stop signal) for stopping the high-frequency current outputted from the high-frequency power supply device 2 to the living tissue side.

Figure 3:
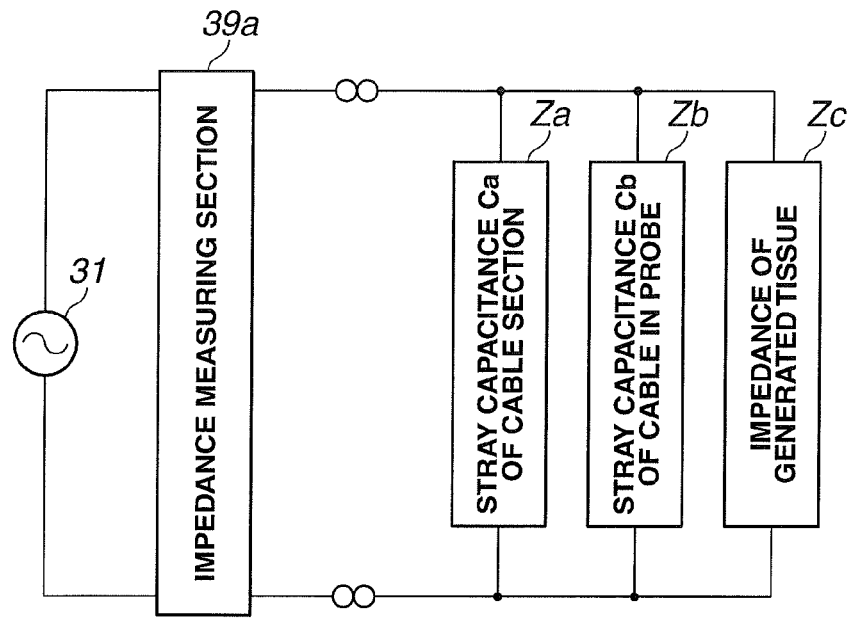
FIG. 3 is a diagram showing an equivalent circuit of a high-frequency treatment instrument and a living tissue.

An equivalent circuit of a high-frequency treatment instrument and a living tissue in a treatment state in which a high-frequency current is fed to the living tissue in this embodiment is as shown in FIG. 3. A frequency of the high-frequency current generated by the high-frequency current generating section 31 in this embodiment is about 350 kHz. In general, in a high-frequency operation apparatus, a frequency of 300 kHz to 500 kHz is used.

The high-frequency current by the high-frequency current generating section 31 is supplied from the electrodes 19a and 19b to the living tissue via cable sections 51 (I=A and B) and the cables 21 in the probe included in the high-frequency treatment instrument. However, the cable sections 51 and the cables 21 in the probe are substantially a stray capacitance with respect to an impedance value of the living tissue.

Therefore, as shown in FIG. 3, the high-frequency treatment instrument and the living tissue functioning as loads to the high-frequency current by the high-frequency current generating section 31 are represented by an equivalent circuit in which an impedance value Za of a stray capacitance Ca by the cable sections 51, an impedance value Zb of a stray capacitance Cb by the cables 21 in the probe 4, and an impedance value (referred to as tissue impedance value) Zl(t) of the living tissue are connected in parallel.

When an imaginary unit j of a transactional theory and an angular frequency co of the high-frequency current are used, the impedance value Za of the stray capacitance Ca and the impedance value Zb of the stray capacitance Cb are represented as $Za=1/(j\omega Ca)$ and $Zb=1/(j\omega Cb)$. Both the stray capacitances Ca and Cb can be combined and represented as one stray capacitance Ca+Cb. In this case, the equivalent circuit is an equivalent circuit in which a tissue impedance value Zl(t) of the living tissue is connected in parallel to an impedance value Zab ($=1/(j\omega(Ca+Cb))$) by the stray capacitance Ca+Cb.

In this embodiment, when the high-frequency current is supplied to the living tissue and the treatment of sealing or coagulation is performed, the impedance value Z(t) on the living tissue side during the treatment is measured by the impedance measuring section 39a provided in the high-frequency power supply device 2 and a progress process of the treatment of sealing or coagulation is monitored.

In this case, an impedance value actually measured by the impedance measuring section 39a is a combined impedance value Z(t) of the impedance value Zab by the stray capacitance Ca+Cb and the tissue impedance value Zl(t) of the parallel connection.

When moisture in the living tissue starts to evaporate through high-frequency heating by the high-frequency current, the tissue impedance value Zl(t) of the living tissue substantially increases.

Figure 4:
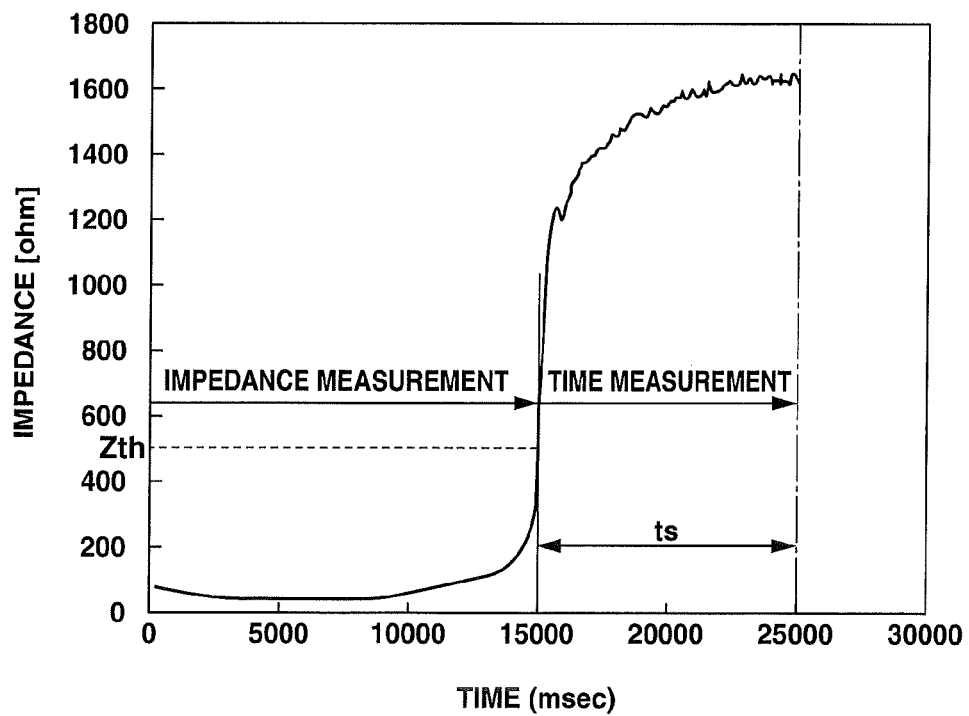
FIG. 4 is a diagram showing a representative example of a change in an impedance value measured by an impedance measuring section in a state in which a high-frequency current is supplied to the living tissue.

FIG. 4 shows a characteristic example of a temporal change of the impedance value Z(t) measured by the impedance measuring section 39a when the high-frequency current is supplied to the living tissue and the treatment is performed.

The horizontal axis in FIG. 4 indicates an output time of the high-frequency current with 0 set as time when the high-frequency current is supplied and the treatment is started. The vertical axis indicates the impedance value Z(t).

When the treatment is performed by the high-frequency treatment instrument, as the cable sections 51 and the probe 4, those having cable length and sheath length different according to treatment are used. For example, in the case of an abdominal operation, those having sheath length of about 100 mm are generally used. In a laparoscopic operation, those having sheath length of about 300 mm is generally used.

In the probe 4 of the same type, there is fluctuation of a maximum degree of 30% among products. Therefore, a value of the stray capacitance Ca+Cb in FIG. 3 changes. When an average of values of the stray capacitance Ca+Cb is roughly evaluated, the average is often about 300 pF.

On the other hand, the tissue impedance value Zl(t) of the living tissue rapidly increases from a state of an initial value of 200 to 300Ω when moisture in the living tissue starts to evaporate and dehydrate. The tissue impedance value Zl(t) increases from a value of the initial value to about 1000 to 1500Ω, which is a value several times as large as the value of the initial value or more, in a short time. Therefore, the detecting section 39b may determine that the tissue impedance value Zl(t) reaches the impedance threshold when the tissue impedance value Zl(t) is an impedance value several times as large as an initial impedance value of the living tissue measured by the impedance measuring section 39a at the time of the start of the supply of the high-frequency current.

FIG. 4 shows a representative example of the impedance value Z(t) measured by the impedance measuring section 39a when the stray capacitance Ca+Cb is included. FIG. 4 represents a characteristic that the tissue impedance value Zl(t) of the living tissue changes from the value of the initial value to the value several times as large as the initial value or more in a short time near time (about 15000 ms) when moisture in the living tissue starts to evaporate and dehydrate.

In a conventional example, the output of the high-frequency current is stopped at timing when the impedance value Z(t) measured by the impedance measuring section 39a reaches a predetermined impedance value in a state in which coagulation for the living tissue ends.

However, the impedance measuring section 39a measures the combined impedance value Z(t) with the tissue impedance value Zl(t) connected in parallel to the stray capacitance Ca+Cb. Therefore, an impedance value by the stray capacitance Ca+Cb with respect to the tissue impedance value Zl(t) becomes an error and substantially affects measurement accuracy, in particular, in a high impedance region.

Figure 5:
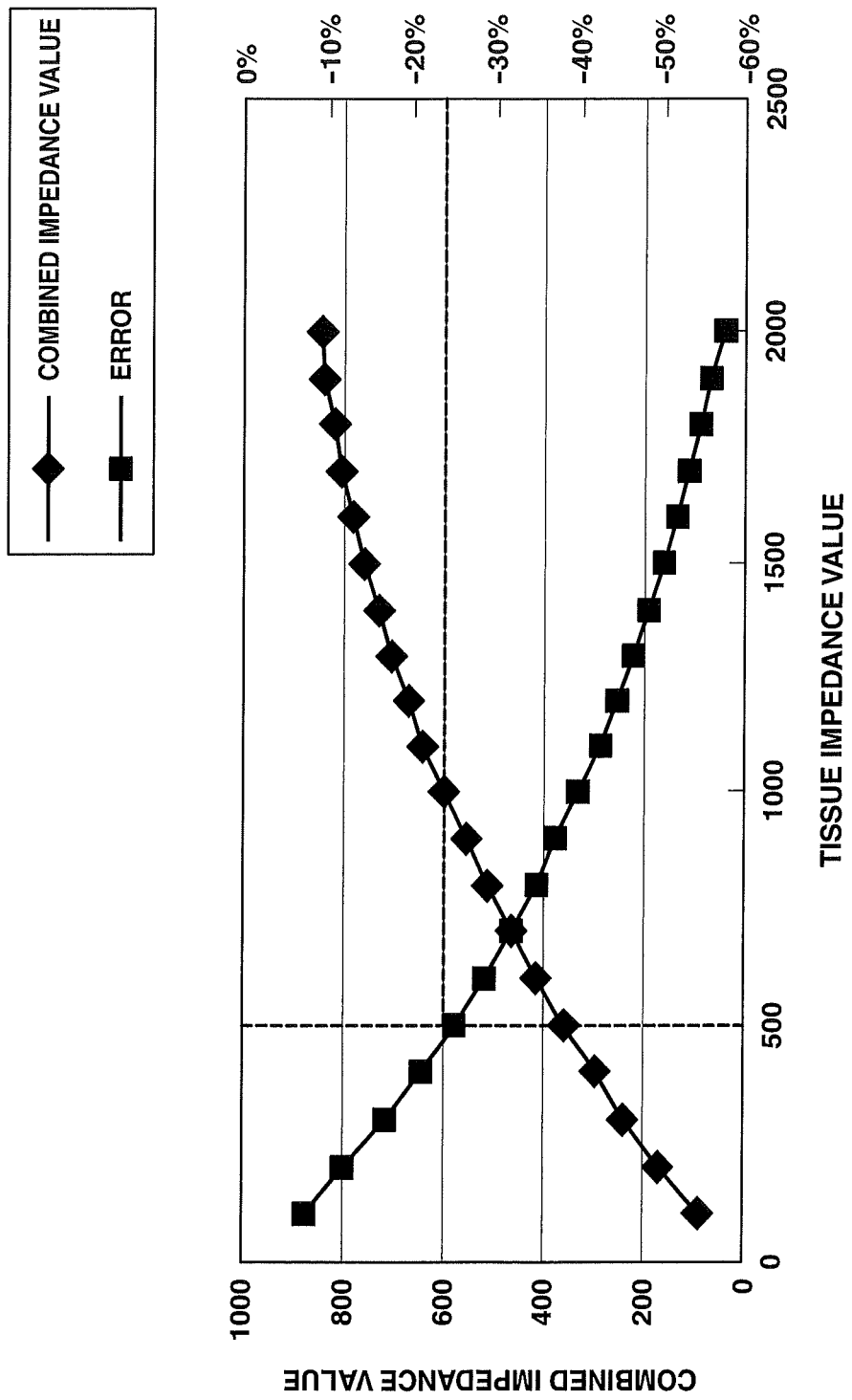
FIG. 5 is a diagram showing a degree of an error due to a combined impedance value and a stray capacitance with respect to a tissue impedance value of the living tissue.

FIG. 5 shows a combined impedance value and a degree of an error in the case in which a value of the stray capacitance Ca+Cb is set to, for example, about 300 pF and a value of the impedance value Zab by the stray capacitance Ca+Cb is regarded as an error with respect to the tissue impedance value Zl.

As it is seen from FIG. 5, in a region where the tissue impedance value Zl is small, the combined impedance value can be measured (detected) with a relatively small error. However, in a high impedance region where the tissue impedance value Zl is large, it is difficult to measure the combined impedance value with a small error.

From a characteristic shown in FIG. 5, for example, when it is attempted to measure the combined impedance with an error within 25%, the tissue impedance value Zl is in a range of impedance equal to or smaller than 500Ω (100Ω to 500Ω) as indicated by a dotted line.

On the other hand, when, as in the conventional example, the combined impedance value is measured and it is determined whether the measured combined impedance value reaches a predetermined impedance value in a state in which coagulation is completed, the predetermined impedance value is set to about 1500 to 2000 a Therefore, it is highly likely that a large error exceeding 50% occurs.

In this way, in the method of the conventional example, because of the stray capacitance Ca+Cb, it is difficult to accurately measure whether the measured combined impedance value reaches the predetermined impedance value in the state in which coagulation is completed.

Therefore, in this embodiment, the impedance measuring section 39a does not directly measure the measured combined impedance value in the state in which the coagulation is completed, as accuracy of the measurement is predicted to be deteriorated. Rather, the impedance measuring section 39a measures whether the measured combined impedance value reaches the impedance threshold Zth in the state before the coagulation is completed at the time when moisture in the living tissue starts to evaporate. Accuracy of the measurement is higher. The impedance threshold Zth in this case is set in a range of 100Ω to 500Ω. This makes it possible to accurately measure whether the measured combined impedance value reaches the impedance threshold Zth.

When the measured impedance value Z(t) reaches the impedance threshold Zth, the specific time ts required from this time until the state in which coagulation is completed is measured by a time measuring section 41a of the timer 41. When the specific time ts is measured, the output control section 39c performs control for stopping the output of the high-frequency current.

In this embodiment, the specific time ts is actually set to a value obtained by adding a margin time to time required from the time when moisture in the living tissue starts to evaporate until coagulation is completed.

The specific time ts is set according to size of a treatment target living tissue, a moisture content contained in the living tissue, and a grasping area for grasping the living tissue in the probe 4 in use. The specific time ts is set within a range of 100 ms to 20000 ms according to the size, the moisture content, and the grasping area.

For example, the upper limit value 20000 ms is set in order to make it possible to sufficiently perform the treatment of coagulation even when length of the grasping portion of the probe 4 is 50 mm, width of the grasping section is 10 mm, and thickness of the treatment target living tissue is 20 mm, which are maximum conditions.

The surgeon can set the impedance threshold Zth and the specific time ts using the setting section 28.

When a large error is allowed, the impedance threshold Zth can be set in a range wider than 100Ω to 500Ω. For example, when an error of about 50% is allowed, the impedance threshold Zth can be set to about 100Ω to 1500Ω.

An operation for performing treatment for coagulating (sealing), using the probe 4, a living tissue, for example, the blood vessel 18 by the high-frequency operation apparatus 1 according to this embodiment having such a configuration is explained with reference to a flowchart of FIG. 6.

The surgeon turns on the power switch 26 and performs initial setting of a value of high-frequency power, the impedance threshold Zth, the specific time ts, an output mode, and the like in the case of treatment as shown in step S1. The surgeon selects, as the output mode, a continuous output mode for continuously outputting a high-frequency current.

The surgeon grasps the blood vessel 18, which is a treatment target living tissue, using the electrodes 19a and 19b of the treatment section 10 at a distal end portion of the probe 4 shown in FIG. 1. A state in which the blood vessel 18 is grasped by the electrodes 19a and 19b is schematically shown in FIG. 2.

As shown in step S2, the surgeon turns on the foot switch 27 functioning as the output switch in order to perform the treatment of coagulation for the blood vessel 18. The output switch may be provided in the probe 4.

According to the turn-on of the foot switch 27, (the output control section 39c by) the CPU 39 of the control section 38 controls the high-frequency current generating section 31 to generate a high-frequency current. The high-frequency current generating section 31 outputs the high-frequency current from an output end. The cable section 5A and the cables 21 in the probe 4 transmit the high-frequency current and supply the high-frequency current to the blood vessel 18, which is in contact with the electrodes 19a and 19b. The high-frequency current flows to the blood vessel 18 and the treatment of coagulation is started. In other words, an output of the high-frequency current in step S3 in FIG. 3 is started.

At this point, as shown in step S4, the impedance measuring section 39a of the CPU 39 captures the impedance value Z(t) at a predetermined period. In other words, the impedance measuring section 39a starts measurement of the impedance value Z(t).

As shown in the next step S5, the detecting section 39b of the CPU 39 detects (determines) whether the captured impedance value Z(t) reaches the impedance threshold Zth set in advance, i.e., whether Z(t)≥Zth.

If a condition Z(t)≥Zth is not satisfied (i.e., Z(t)<Zth), the CPU 39 continues the processing in step S4.

On the other hand, in the case of a determination result that the condition Z(t)≥Zth is satisfied, the CPU 39 proceeds to processing in step S6. In step S6, the CPU 39 causes the timer 41 to start measurement of an output time for measuring time of completion of coagulation.

The timer 41 starts, from timing when the impedance value Z(t) reaches the impedance threshold Zth, an output time in which the high-frequency current is outputted to the living tissue side.

In the next step S7, the timer 41 or the CPU 39 determines whether the output time reaches the specific time ts.

If the output time does not reach the specific time ts, the timer 41 continues an operation for measuring the output time.

On the other hand, if the output time reaches the specific time ts, in step S8, the output control section 39c of the CPU 39 performs control for stopping the output of the high-frequency current. The CPU 39 performs control for causing the display section 29 to display a message of the completion of the treatment of coagulation. The CPU 39 ends the treatment of coagulation shown in FIG. 6.

The treatment of coagulation (sealing) for the blood vessel 18, which is the living tissue, by the high-frequency operation apparatus 1 is explained above. However, the treatment of coagulation can be applied to a living tissue such as a ligament tissue in the same manner.

According to this embodiment in which the operation is performed as explained above, it is possible to reduce the influence of a stray capacitance due to the lengths and the like of the cable sections 51 and the cables 21 in the probe 4 and appropriately perform the treatment of coagulation for the living tissue.

On the other hand, when only impedance measurement is performed and the output of the high-frequency current is stopped when the measured impedance value Z(t) reaches an impedance threshold set in a state in which the treatment of coagulation is completed (ended), it is difficult to appropriately set a value of the impedance threshold.

Specifically, as shown in FIG. 4, near time when the treatment of coagulation is completed, since a temporal change of the impedance value Z(t) is small, if the impedance threshold is set to a value slightly larger than an impedance value corresponding to the completion of the treatment of coagulation (within a range in which a relative error is not large), actually even after the treatment of coagulation is completed, the high-frequency current sometimes continues to be outputted uselessly (i.e., idle output is performed). In this case, an operation time increases.

Conversely, if the impedance threshold is set to a value slightly smaller than the impedance value corresponding to the completion of the treatment of coagulation (within a range in which a relative error is not large), coagulation is determined as being completed and the output of the high-frequency current is stopped before coagulation is not actually completed. When the impedance threshold is set, it is necessary to take into account a stray capacitance. Therefore, it is difficult to determine only from the impedance measurement that coagulation is completed. The determination tends to be affected by noise.

On the other hand, in a method of performing time measurement from a start of supply (output) of the high-frequency current first and, when measured time reaches an output time threshold set to correspond to the completion of the treatment of coagulation, performing stop of the output of the high-frequency current, it is difficult to appropriately set the output time threshold because of, for example, a value of the high-frequency current.

On the other hand, this embodiment makes use of a characteristic property that a tissue impedance value in a state in which moisture in the living tissue starts to evaporate substantially increases in a short time in a halfway state of the completion of the treatment of coagulation in the living tissue. Therefore, the tissue impedance value can be accurately detected by impedance measurement.

Thereafter, time measurement is performed and, when measured time reaches the specific time ts when the treatment of coagulation is completed, the output of the high-frequency current is stopped. Therefore, it is possible to prevent the high-frequency current from being uselessly outputted after the treatment of coagulation is completed. Further, it is possible to prevent an operation time from increasing.

As a modification of this embodiment, a configuration explained below may be adopted. The time measuring section 41a measures a predetermined time (detection time) tr from time of a start of supply (a start of output) of the high-frequency current to the living tissue side until the detecting section 39b detects that the impedance value Z(t) reaches the impedance threshold Zth at the time when moisture in the living tissue starts to evaporate. The specific time ts is corrected or set according to the predetermined time tr.

It is expected that, according to a value of a high-frequency current used for actual treatment set by the surgeon and thickness and size (width) of a treatment target living tissue, time required from the time when moisture in the living tissue starts to evaporate (the impedance threshold Zth) until the treatment of coagulation is completed is affected by, for example, the value of the high-frequency current.

Therefore, the predetermined time tr is measured as time from the time of the start of the output until the impedance value Z(t) measured by the impedance measuring section 39a reaches the impedance threshold Zth such that the influence can be reduced.

According to the measured predetermined time tr, a correction coefficient tr/trs for correcting the specific time ts before correction is calculated with reference to a predetermined time (a standard time) trs set as a standard value. The specific time ts before correction is corrected by the correction coefficient tr/trs. In this case, the specific time ts before correction is corrected in proportion to a value of the actually-measured predetermined time tr.

Figure 7A:
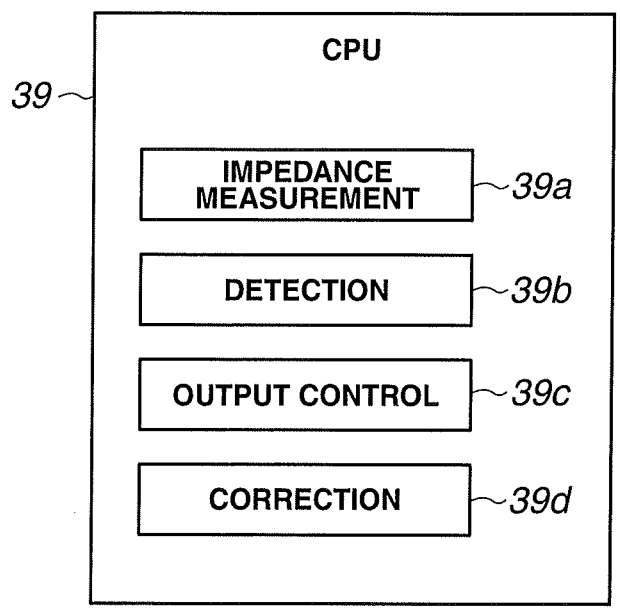
FIG. 7A is a block diagram showing functional blocks of a CPU in a modification of the first embodiment.

The CPU 39 shown in FIG. 7A in the modification in which such correction is performed includes a correcting section 39d in the configuration shown in FIG. 2. The correcting section 39d multiplies the specific time ts before correction with the correction coefficient tr/trs and calculates a specific time ts' after correction. When the time measuring section 41a measures that the output time reaches the specific time ts', the output control section 39c performs control for stopping the output of the high-frequency current.

A procedure of treatment according to this modification is explained. In a procedure of the treatment according to the modification, as shown in FIG. 7B, processing in step S11 is inserted between step S4 and step S5 in the procedure shown in FIG. 6. Steps S12 and S13 are inserted between step S5 and step S6. Step S7 is replaced with step ST in which the specific time ts is replaced with the specific time ts'.

Figure 6:
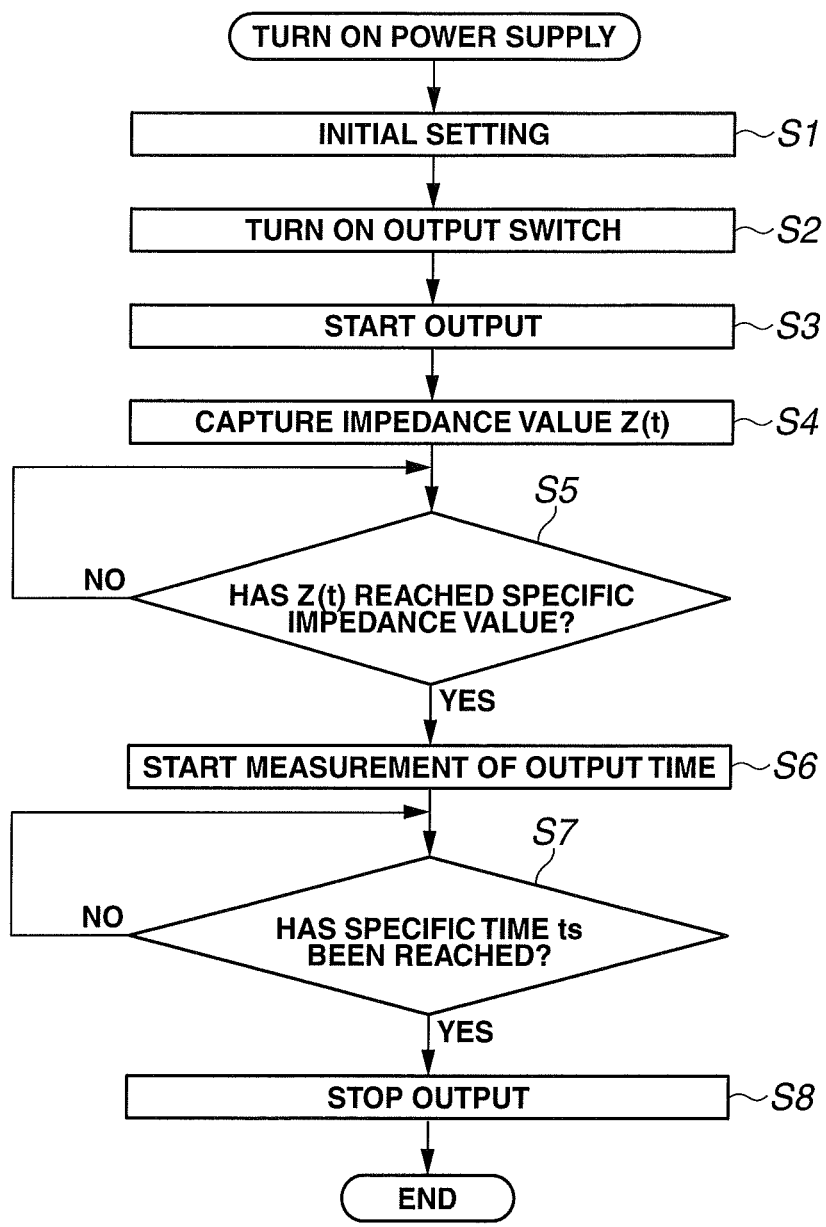
FIG. 6 is a flowchart for explaining a processing procedure for performing an operation of coagulation for a treatment target living tissue according to the first embodiment.

In the case of this modification, the processing from step S1 to step S4 is performed in the same manner as the case of FIG. 6.

When the output switch is turned on in step S2, an output is started in step S3. In the next step S4, capturing of the impedance value Z(t) is started. Simultaneously with the processing in step S4, in step S11, the time measuring section 41a of the timer 41 starts time measurement. The timer 41 performs measurement of an output time in the same manner as the measurement of an output time in step S6 explained below. Therefore, the measurement of an output time in step S6 explained below can be regarded as measurement of a first output time. Step S11 can be regarded as measurement of a second output time.

In the next step S5, the detecting section 39b detects whether the measured impedance value Z(t) reaches a specific impedance value, i.e., the impedance threshold Zth. If the impedance value Z(t) reaches the impedance threshold Zth, in step S12, the time measuring section 41a of the timer 41 further acquires a value of the predetermined time tp in that case.

Further, in the next step S13, the correcting section of the CPU 39 corrects the specific time ts (before correction) with the correction coefficient tp/tps and sets the specific time ts'.

In the next step S6, the time measuring section 41a starts measurement of an output time from time when the impedance value Z(t) reaches the impedance threshold Zth.

In the next step S7', the output control section 39c measures whether the measured output time reaches the specific time ts'. When the measured output time reaches the specific time ts', as shown in step S8, the output control section 39c stops the output.

According to this modification, even when a value of a high-frequency current and thickness and size of a treatment target living tissue in the case of treatment are different, it is possible to reduce the influence of the difference and perform smooth treatment. Besides, the modification has effects same as the effects of the first embodiment.

Second Embodiment

Figure 8:
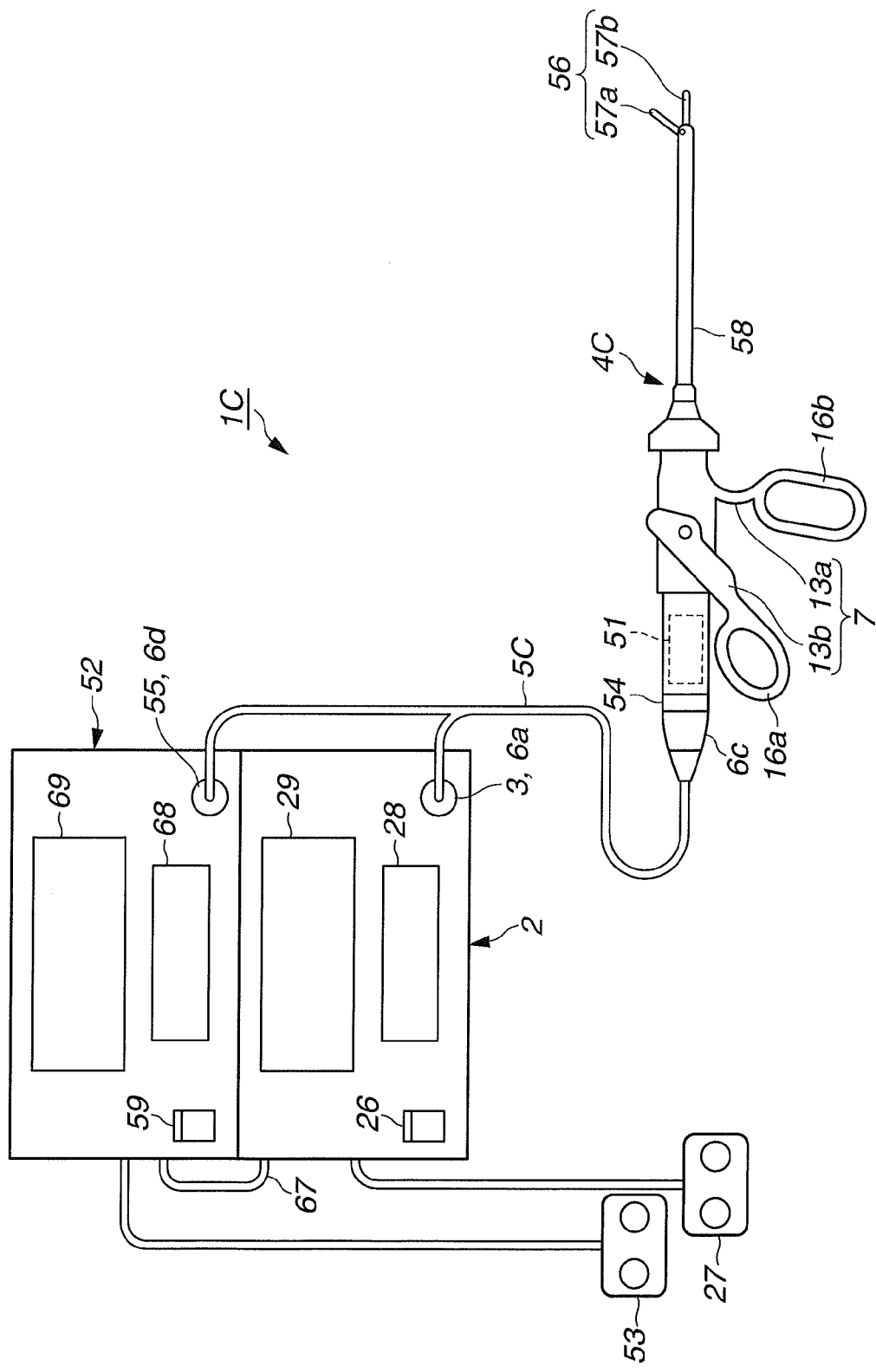
FIG. 8 is a diagram showing an overall configuration of an operation apparatus according to a second embodiment of the present invention.

A second embodiment of the present invention is explained. FIG. 8 shows an operation apparatus 1C according to the second embodiment of the present invention. In the first embodiment, the high-frequency operation apparatus 1 performs the treatment of coagulation by the high-frequency current. However, the operation apparatus 1C according to this embodiment performs treatment of coagulation and separation for a treatment target living tissue such as a blood vessel simultaneously using a high-frequency current and ultrasound vibration. The treatment from coagulation to separation can be performed in a short time by using both of the high-frequency current and the ultrasound vibration.

The operation apparatus 1C according to this embodiment further includes, instead of the probe 4 including the treatment function by a high-frequency current in the first embodiment (including the high-frequency power supply device 2), a probe 4C functioning as a high-frequency and ultrasound treatment instrument incorporating an ultrasound transducer 51 that ultrasonically vibrates and including (the treatment function by a high-frequency current and) a treatment function by ultrasound vibration.

The operation apparatus 1C includes an ultrasound driving power supply device 52 that supplies an ultrasound driving signal for causing the ultrasound transducer 51 to ultrasonically vibrate to the ultrasound transducer 51. A foot switch 53 functioning as an output switch for performing ON and OFF of an output of an ultrasound driving signal is connected to the ultrasound driving power supply device 52.

In this embodiment, connectors 6a and 6d at the other end of a cable section 5C, a connector 6c of which is connected to a connector 54 of the probe 4C, are respectively connected to the connector bearing 3 of the high-frequency power supply device 2 and a connector bearing 55 of the ultrasound driving power supply device 52. In FIG. 8, as the cable section 5C, one cable is divided into two cables halfway. The connectors 6a and 6d are provided at respective ends of the two cables. However, the cable section 5C may be formed of two cables.

In this embodiment, as in the first embodiment, an operation can also be performed using a cable section (not shown) having cable length different from cable length of the cable section 5C. A probe having sheath length different from sheath length of the probe 4C shown in FIG. 8 can also be used.

The connector 6d of the cable section 5C is connected to the connector bearing 55 of the ultrasound driving power supply device 52, whereby, in a state in which a power switch 59 is turned on, the ultrasound driving power supply device 52 supplies an ultrasound driving signal to the ultrasound transducer 51 via a cable 23' (see FIG. 9) of the cable section 5C and causes the ultrasound transducer 51 to ultrasonically vibrate.

In the probe 4C, the handles 13a and 13b respectively including the finger holding sections 16a and 16b are provided in the operation section 7 as in the case of the probe 4. However, in the probe 4C, only one (specifically, 57a) of treatment members 57a and 57b, which form a treatment section 56 provided at a distal end of a sheath 58, is opened and closed with respect to the treatment member 57b according to opening and closing on the handle 13b side with respect to the handle 13a.

Figure 9:
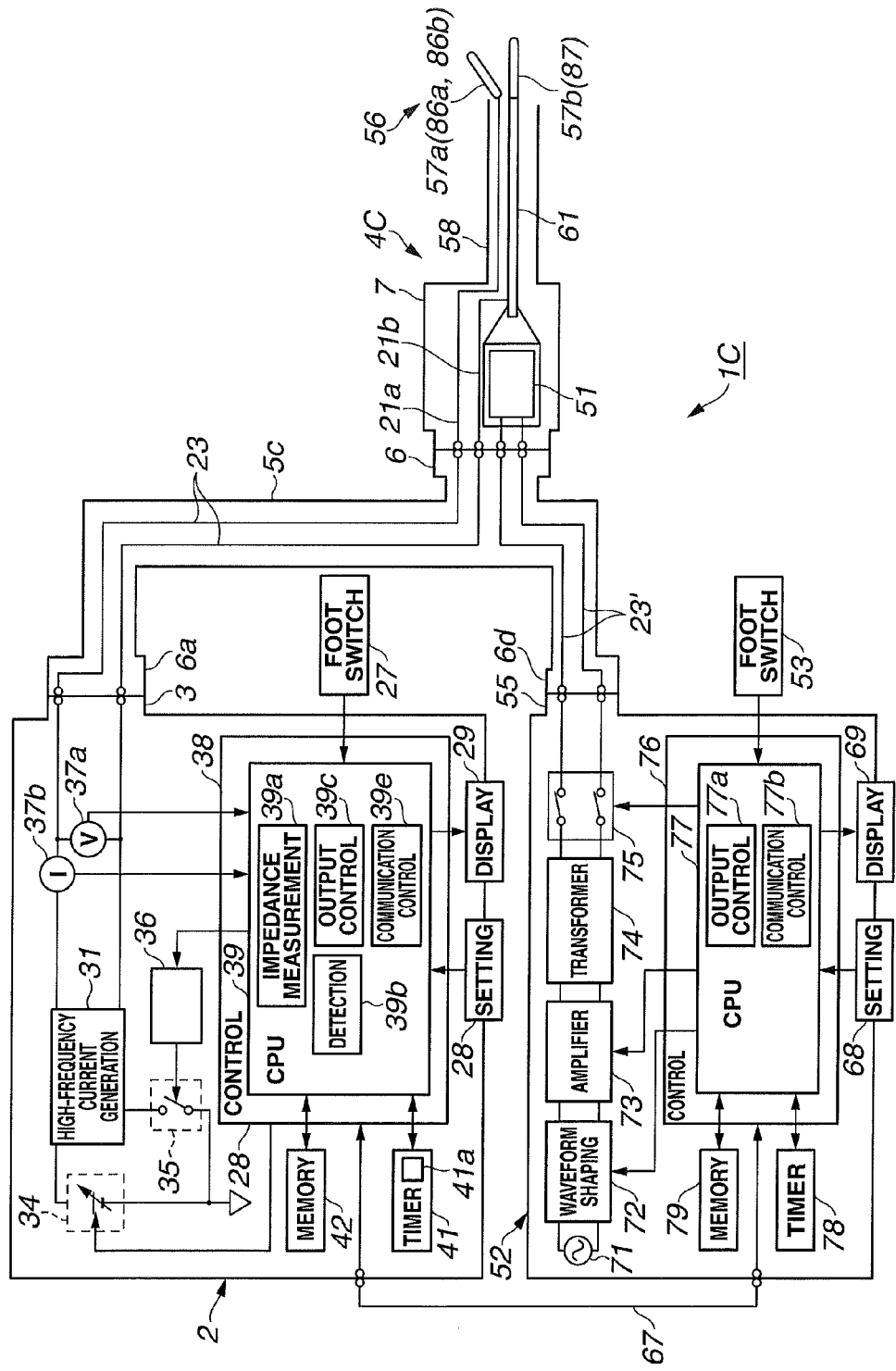
FIG. 9 is a block diagram showing an internal configuration of a high-frequency power supply device and an ultrasound driving power supply device in the operation apparatus.

As explained above, the ultrasound transducer 51 ultrasonically vibrates according to the ultrasound driving signal. As shown in FIG. 9, the ultrasound vibration by the ultrasound transducer 51 is transmitted to the treatment member 57b at a distal end thereof by an ultrasound transmitting member 61 that is arranged in the sheath 58 and a proximal end of which is coupled to the ultrasound transducer 51.

The ultrasound vibration by the treatment member 57b is supplied to a living tissue grasped by the treatment members 57a and 57b. Therefore, the ultrasound transducer 51, the ultrasound transmitting member 61, and the treatment member 57b form an ultrasound supplying section that supplies the ultrasound vibration to the living tissue. In a narrow sense, the treatment member 57b forms an ultrasound supplying section that supplies the ultrasound vibration to the living tissue.

A high-frequency current by the high-frequency power supply device 2 is transmitted to electrodes at distal ends via the cable 23 in the cable section 5C and the cables 21a and 21b in the probe 4C. In the treatment member 57a, as shown in FIG. 12C and the like referred to below, electrodes 86a and 86b are provided on both sides of a pad member 83 in a center. In the treatment member 57b, an electrode 87 opposed to the electrodes 86a and 86b is formed. A part of the cable 21b is used by the ultrasound transmitting member 61 as well. However, a configuration may be adopted in which the part of the cable 21b is not used by the ultrasound transmitting member 61.

As shown in FIG. 8, in the ultrasound driving power supply device 52, as in the high-frequency power supply device 2, a setting section 68 for setting, for example, a value of an ultrasound output and a display section 69 for performing various kinds of display are provided.

The high-frequency power supply device 2 and the ultrasound driving power supply device 52 are connected by a communication cable 67 for performing communication.

As shown in FIG. 9, an oscillation circuit 71 is provided in the ultrasound driving power supply device 52. An oscillation signal of the oscillation circuit 71 is inputted to a waveform shaping circuit 72 that shapes the oscillation signal into a signal having a waveform suitable for performing treatment of coagulation, separation, and the like. An output signal of the waveform shaping circuit 72 is inputted to a transformer 74 after being amplified by an amplifier 73. The transformer 74 insulates the input signal from the output signal and boots the input signal and outputs the input signal as an ultrasound driving signal.

The ultrasound driving signal is outputted to the high-frequency and ultrasound treatment instrument side connected to the connector bearing 55 via a switch circuit 75 for performing ON and OFF of the signal. The connector 6d of the cable section 5C is connected to the connector bearing 55, whereby the ultrasound driving signal is supplied (applied) to the ultrasound transducer 51 of the probe 4C. The ultrasound transducer 51 ultrasonically vibrates.

In the ultrasound driving power supply device 52, a CPU 77 included in a control section 76 that controls operations of the waveform shaping circuit 72, the amplifier 73, the switch circuit 75, and the like is provided.

The CPU 77 is connected to the foot switch 53, a timer 78 that performs time measurement, and a memory 79 that stores various kinds of information and the like.

The CPU 77 has a function of an output control section 77a that performs ON and OFF of the switch circuit 75 according to instruction operation for an output instruction and an output stop of the foot switch 53. The CPU 77 performs control corresponding to output setting by the setting section 68.

The CPU 39 and the CPU 77 have functions of communication control sections 39e and 77b that can transmit and receive signals to and from each other through the communication cable 67 and perform an operation of the other device in association (synchronization) with an operation of one device.

In this embodiment, for example, the CPU 39 included in the control section 38 of the high-frequency power supply device 2, which is one device in both the devices, transmits a control signal or the like to the ultrasound driving power supply device 52 via the communication cable 67 included in a communication section and controls an operation of the ultrasound driving power supply device 52 in association with an operation of the high-frequency power supply device 2.

For example, when the function of the associated operation is set to ON by the communication control sections 39*e* and 77*b*, if the foot switch 27 is turned on or off, an output start or an output stop of the high-frequency power supply device 2 and the ultrasound driving power supply device 52 can be performed. Control of operations of both the devices can be performed by instruction operation of only one foot switch 27.

In this embodiment, information concerning a specific time ts2 required from timing when the impedance value Z(t) reaches the impedance threshold Zth at the time when moisture in the living tissue starts to evaporate until the living tissue is separated is stored in the memory 42.

Figure 10:
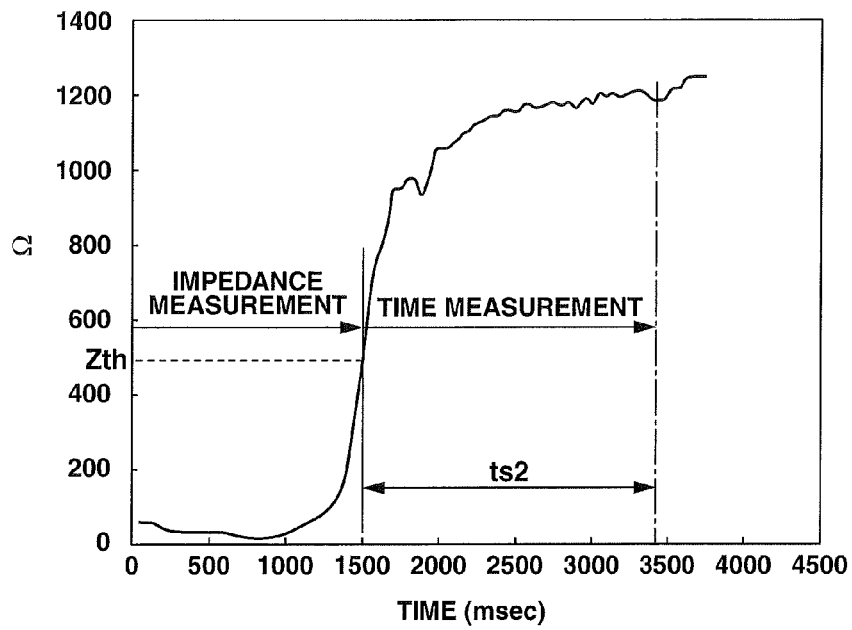
FIG. 10 is a diagram showing a representative example of a change in an impedance value measured by an impedance measuring section in a state in which a high-frequency current and ultrasound vibration are supplied to a living tissue.

FIG. 10 shows a representative example of a change in the impedance value Z(t) measured by the impedance measuring section 39*a* in a state in which coagulation and separation are applied to the living tissue in this embodiment.

In this embodiment, when treatment is started as in the first embodiment, the impedance measuring section 39*a* measures the impedance value Z(t) on the living tissue side. The detecting section 39*b* detects that the impedance value Z(t) reaches the impedance threshold Zth at the time when moisture in the living tissue starts to evaporate.

In the example shown in FIG. 10, the impedance measurement is performed from time when the treatment is started (i.e., high-frequency and ultrasound output start). The detecting section 39*b* detects that the impedance value Z(t) reaches the impedance threshold Zth (in FIG. 10, the impedance value Z(t) reaches the impedance threshold Zth at a time near 1500 ms from the start of the treatment).

The time measuring section 41*a* of the timer 41 measures the specific time ts2 from timing when it is detected that the impedance value Z(t) reaches the impedance threshold Zth at the time when moisture in the living tissue starts to evaporate until the living tissue is separated. When measured time reaches the specific time ts2, the output control section 39*c* of the CPU 39 stops the output of the high-frequency current. In the example shown in FIG. 10, time near 3400 ms is the specific time ts2.

In short, as explained in the first embodiment, in this embodiment, in the case of the impedance measurement, the impedance measurement is not performed in a high impedance region in which a large error is predicted. Measurement of time until separation is completed is performed.

The specific time ts2 is set to include time required from the time when moisture in the living tissue starts to evaporate until coagulation is completed and separation is completed.

Figure 11:
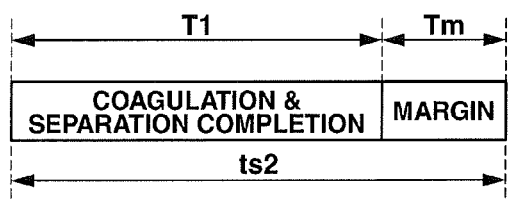
FIG. 11 is a diagram showing a setting example of a specific time.

FIG. 11 shows a setting example of the specific time ts2. For a treatment target living tissue (e.g., a ligament tissue, a blood vessel, or a pellicle tissue), the specific time ts2 is set to a value obtained by adding a margin time Tm (for further continuing treatment in order to ensure separation completion) to time T1 required from the time when moisture in the living tissue starts to evaporate until coagulation is completed and separation is completed. In the first embodiment, the specific time ts is set to a value obtained by adding a margin time to time required from the time when moisture in the living tissue starts to evaporate until coagulation is completed.

The time T1 required until separation is completed through completion of coagulation is statistically different values when the living tissue is, for example, the ligament tissue, the blood vessel, and the pellicle tissue. Therefore, the surgeon may set the specific time ts2 using the setting section 28 according to a living tissue to be actually treated.

In this embodiment, the impedance threshold Zth is set in a range of impedance equal to or smaller than 500Ω (100Ω to 500Ω) as in the first embodiment. However, since ultrasound is also used, the specific time ts2 is set in a range (100 ms to 10000 ms) narrower than the range in the first embodiment.

When the output of the high-frequency current is stopped, the communication control section 39*e* of the CPU 39 transmits a control signal for stopping the output to the CPU 77 via the communication cable 67. The CPU 77 stops the output of the ultrasound driving signal. The ultrasound transducer 51 stops the ultrasound vibration. Therefore, in a broad sense, the CPU 39 (the CPU 77 in a narrow sense) performs control for causing the living tissue to stop the ultrasound vibration.

Figure 12A:
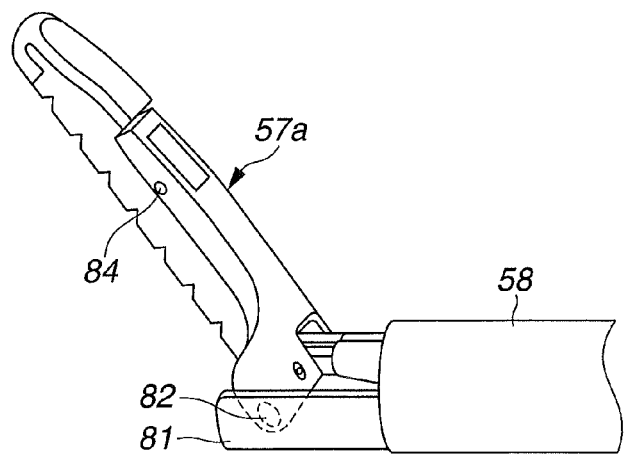
FIG. 12A is a perspective view showing a treatment member on a distal end side of a probe in the second embodiment.
Figure 12B:
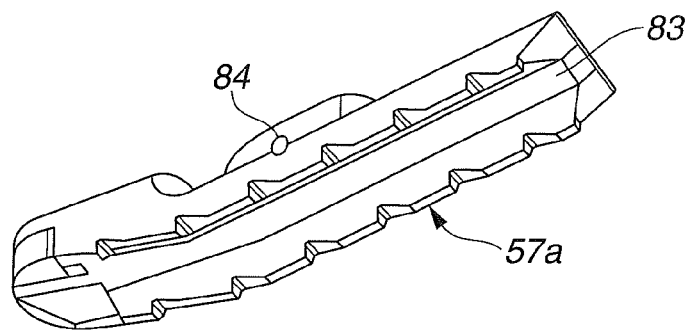
FIG. 12B is a perspective view showing structure on an inner side of the treatment member shown in FIG. 12A.
Figure 12C:
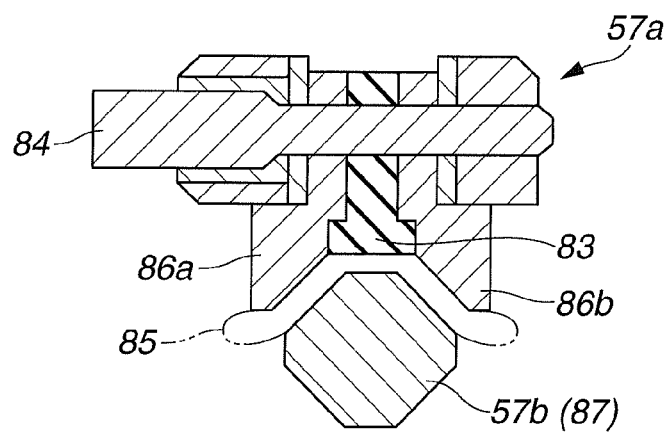
FIG. 12C is a cross sectional view in the case in which a living tissue is grasped by a pair of treatment members to perform treatment of coagulation and separation.
Figure 12D:
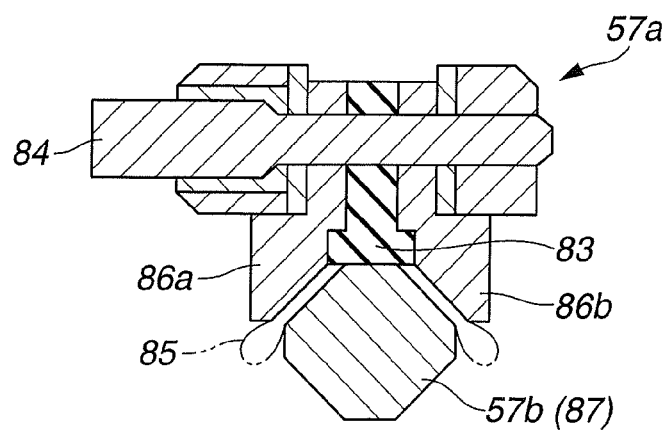
FIG. 12D is a cross sectional view in a state in which the treatment progresses from a state shown in FIG. 12 and the treatment of the separation is completed.

FIGS. 12A and 12B show a configuration of the treatment member 57*a* on the distal end side of the probe 4C. FIGS. 12C and 12D show a transverse section in a position of a fixing screw 84. As shown in these figures, projecting piece 81 projecting to left and right in a pair are provided at a distal end portion of the sheath 58. A proximal end portion of the treatment member 57*a* is pivotably attached to the projecting pieces 81 via a fulcrum pin 82. In FIGS. 12A and 12B, the treatment member 57*b* projecting from an inner side to a distal end side of the sheath 58 is not shown.

As shown in FIG. 12B, in a groove portion provided in a longitudinal direction of the treatment member 57*a* on an inner side of the treatment member 57*a*, i.e., an inner side opposed to (the upper surface of) the treatment member 57*b*, a pad member (a tissue pad) 83 formed of an insulator for grasping a living tissue between the treatment member 57*a* and the ultrasonically-vibrating treatment member 57*b* and applying treatment of coagulation and separation to the living tissue is provided. The pad member 83 is fixed to the treatment member 57*b* by the fixing screw 84. The treatment member 57*b* may be formed of plural members.

In this embodiment, the ultrasonically-vibrating treatment member 57*b* and the pad member 83 apply treatment by ultrasound vibration to a living tissue 85 indicated by an alternate long and two short dashes line grasped between the treatment members 57*a* and 57*b* opposed to each other in an up down direction as shown in FIG. 12C.

In this embodiment, treatment of cauterization by a high-frequency current supplied to a living tissue by the electrodes 86*a* and 86*b* in the treatment member 57*a* on both sides of the pad member 83 and the conductive electrode 87 formed by the treatment member 57*b* opposed to both the electrodes 86*a* and 86*b* can be performed together with the treatment by the ultrasound vibration.

In FIG. 12C, a state immediately before separation applied to the living tissue 85 ends is shown. When the separation is completed, as shown in FIG. 12D, grasping surfaces of the pad member 83 and an upper surface of the treatment member 57*b* are in contact with each other. In this case, small gaps (clearances) are formed between the electrode 86*a* on both sides of the grasping surfaces and the electrode 87 by the treatment member 57*b* and between the electrode 86*b* and the electrode 87.

A more detailed configuration concerning a peripheral portion of the treatment member 57*a* on the distal end side of the sheath 58 is described in, for example, Japanese Patent Application Laid-Open Publication No. 2009-160404.

If the ultrasound vibration is further continued for a long time in a state in which the separation is completed as shown in FIG. 12D, the pad member 83 and the treatment member 57b in a portion forming the grasping surface opposed to the pad member 83 are worn or damaged.

When the treatment is actually performed, even if the separation is completed, the surgeon sometimes cannot visually recognize the completion of the separation of the living tissue 85 and continues the ultrasound output because, for example, the living tissue 85 sticks to the electrodes 86a, 86b, and 87. Consequently, the members forming the grasping surfaces for performing coagulation, separation, and the like are worn or damaged.

In this embodiment, the ultrasound output is prevented from continuing for a long time in a no-load state by performing time measurement without performing impedance measurement. Consequently, it is possible to effectively prevent wear and damage of the members for performing coagulation and separation.

Next, operations of coagulation and separation applied to a living tissue using a high-frequency current and ultrasound vibration by the probe 4C according to this embodiment are explained with reference to FIG. 13.

The surgeon turns on the power switch 26 and performs, in the case of treatment as shown in step S21, initial setting of a value of high-frequency power, a power value of an ultrasound driving signal, an output mode of a high-frequency current, a waveform of the ultrasound driving signal, the impedance threshold Zth, and the specific time ts2.

The surgeon grasps a treatment target living tissue using the treatment section 56 at the distal end portion of the probe 4C. The surgeon turns on the foot switch 27 functioning as the output switch in order to perform treatment as shown in step S22.

According to the turn-on of the foot switch 27, (the output control section 39c by) the CPU 39 of the control section 38 controls the high-frequency current generating section 31 to generate a high-frequency current. The high-frequency current generating section 31 outputs the high-frequency current from an output end. The cable 23 in the cable section 5C and the cables 21 in the probe 4C transmit the high-frequency current and supply the high-frequency current to the living tissue that is in contact with the treatment members 57a and 57b also functioning as electrodes.

The CPU 39 transmits a control signal for turning on an output to the CPU 77 of the ultrasound driving power supply device 52 via the communication cable 67. The CPU 77 turns on the switch circuit 75 and controls the transformer 74 to output an ultrasound driving signal. The ultrasound driving signal is supplied to the ultrasound transducer 51. The ultrasound transducer 51 ultrasonically vibrates and supplies the ultrasound vibration to the living tissue using the treatment member 57b at the distal end of the transducer 51 via the ultrasound transmitting member 61.

In this way, as shown in step S23, the output of the high-frequency current and the ultrasound vibration to the living tissue is started and the treatment for the living tissue is started.

At this point, as shown in step S24, the impedance measuring section 39a of the CPU 39 captures the impedance value Z(t) at a predetermined period. In other words, the impedance measuring section 39a starts measurement of the impedance value Z(t).

As shown in the next step S25, the detecting section 39b of the CPU 39 detects (determines) whether the captured impedance value Z(t) reaches the impedance threshold Zth set in advance, i.e., whether Z(t)≥Zth.

If a condition Z(t)≥Zth is not satisfied (i.e., Z(t)<Zth), the CPU 39 continues the processing in step S24.

On the other hand, in the case of a determination result that the condition Z(t)≥Zth is satisfied, the CPU 39 proceeds to processing in step S26. In step S26, the CPU 39 causes the timer 41 to start measurement of an output time.

The timer 41 starts to measure, from timing when the impedance value Z(t) reaches the impedance threshold Zth, an output time in which the high-frequency current and the ultrasound vibration are outputted to the living tissue side.

In the next step S27, the time measuring section 41a of the timer 41 or the CPU 39 determines whether the output time reaches the specific time ts2.

If it is determined that the output time does not reach the specific time ts2, the CPU 39 continues an operation for measuring the output time.

On the other hand, if it is determined that the output time reaches the specific time ts2, in step S28, the output control section 39c of the CPU 39 performs control for stopping the output of the high-frequency current. The output control section 39c of the CPU 39 transmits a control signal for stopping the output of the ultrasound driving signal to the CPU 77 via the communication cable 67. The CPU 77 turns off the switch circuit 75 and stops the output of the ultrasound driving signal. The ultrasound transducer 51 stops the ultrasound vibration.

The CPU 39 performs control for causing the display section 29 to display a message of the completion of the treatment of coagulation and separation. The CPU 39 ends the treatment shown in FIG. 13.

According to this embodiment, it is possible to perform the treatment of coagulation and separation for the treatment target living tissue in a short time and perform the ultrasound output without continuing the ultrasound output for a long time after the completion of separation. Therefore, it is also possible to reduce wear and damage of the pad members 83 and the like that perform coagulation and separation by the ultrasound vibration.

In this embodiment, as an effect similar to the effect of the first embodiment, it is possible to reduce the influence of a stray capacitance due to, for example, length of the cable section 5C and the cables 21 in the probe 4C and appropriately perform the treatment of coagulation and separation for the living tissue.

In this embodiment, as in the modification of the first embodiment, the predetermined time tp may be acquired by time measurement and a specific time ts2' obtained by correcting the specific time ts2 with the acquired predetermined time tp may be set.

Figure 13:
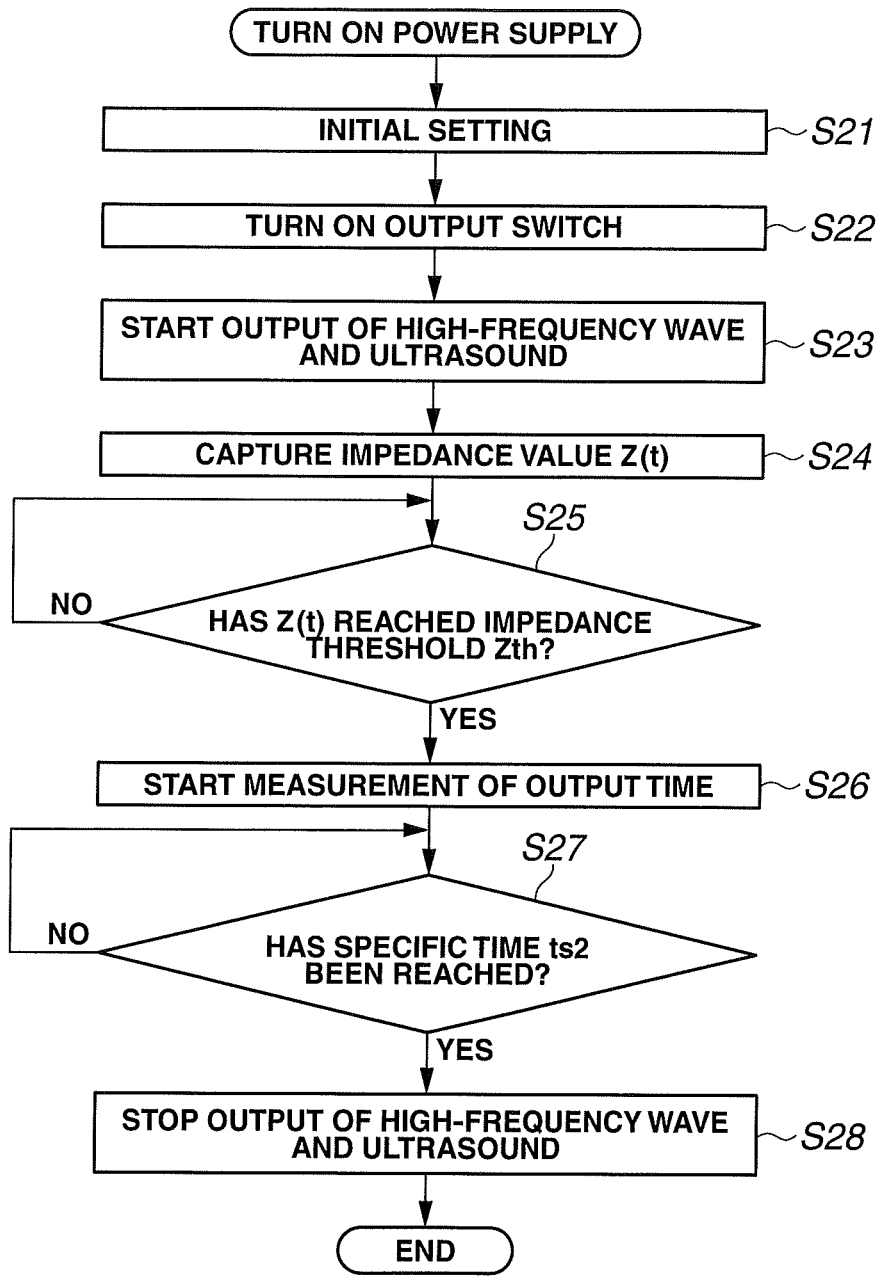
FIG. 13 is a flowchart for explaining a processing procedure for performing operations of coagulation and separation for a treatment target living tissue according to the second embodiment.
Figure 14:
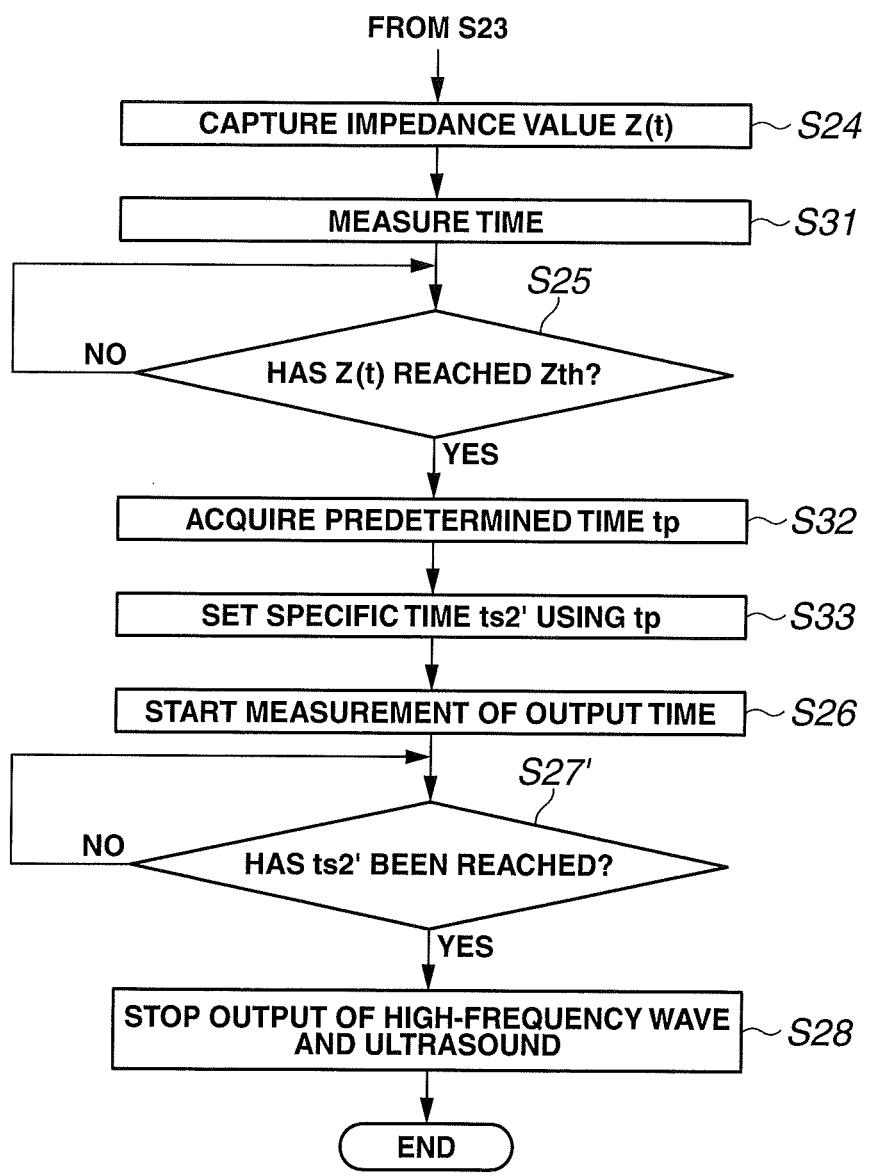
FIG. 14 is a flowchart for explaining a part of a processing procedure in a modification of the second embodiment.

A processing procedure in this case is as shown in FIG. 14. In the processing procedure shown in FIG. 14, step S31 for performing time measurement is inserted between steps S24 and S25 in FIG. 13. Step S32 for acquiring the predetermined time tp and step S33 for setting the specific time ts2' using the predetermined time tp are inserted after steps S25 and S26 in FIG. 13. Step S27 in FIG. 13 is replaced with step S27' in which the specific time ts2 in step S27 is replaced with the specific time ts2'.

As action in this modification, the treatment of coagulation by only the high-frequency current in the case of the modification in the first embodiment is read as the treatment of coagulation and separation by the high-frequency current and the ultrasound vibration and the completion of coagulation is read as the completion of separation.

More specifically, step S21 to step S24 are the same as the steps in the case of FIG. 13. In step S24, the impedance measuring section 39a of the CPU 39 captures the impedance value Z(t) at a predetermined period. Simultaneously with this processing, in step S31, the time measuring section 41a of the timer 41 starts time measurement.

According to the processing in step S25, the detecting section 39b detects that the measured impedance value Z(t) reaches the impedance threshold Zth. When this detection is performed, as shown in step S32, the timer 41 acquires measured time as the predetermined time tp. In step S33, the correcting section formed by the CPU 39 corrects the specific time ts2 using the acquired predetermined time tp and sets the specific time ts2'. In step S26, the timer 41 performs measurement of an output time. Step S26 is processing for measuring an output time from time of detection by the detecting section 39b until separation is completed.

Processing after step S26 is the same as the processing shown in FIG. 13. However, as a specific time in step S27', ts2' is used.

According to this modification, even when a value of a high-frequency current, a value of an ultrasound output, and thickness and size of a treatment target living tissue in the case of treatment are different, it is possible to reduce the influence of the difference and perform smooth treatment. Besides, the modification has effects same as the effects of the second embodiment.

Near the time when moisture in the living tissue starts to evaporate, the tissue impedance value Zl(t) of the living tissue exhibits a characteristic that the tissue impedance value Zl(t) suddenly increases in a short time. A region where this characteristic is exhibited is shown as an impedance changing region R in FIG. 15B.

Figure 15A:
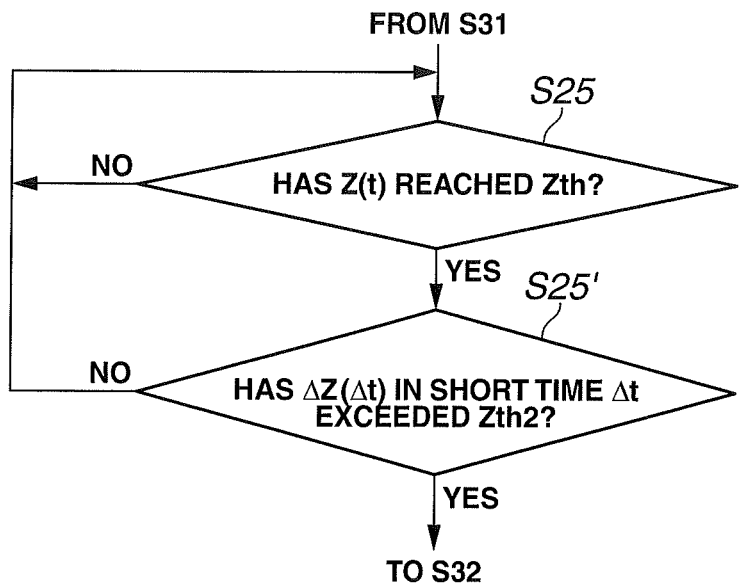
FIG. 15A is a flowchart for explaining processing in which step S25 in FIG. 14 is modified.

For example, when the detecting section 39b detects that the impedance value Z(t) measured by the impedance measuring section 39a reaches the impedance threshold Zth in step S25 in FIG. 14, processing shown in FIG. 15A may be performed making use of the characteristic of the impedance changing region R.

In FIG. 15A, if it is detected in step S25 that the impedance value Z(t) reaches the impedance threshold Zth, in step S25', the detecting section 39b further detects whether an impedance change amount $\Delta Z(\Delta t)$, which is a change amount of the measured impedance value Z(t) in a short time $\Delta t$, changes more than the second impedance threshold Zth2.

Figure 15B:
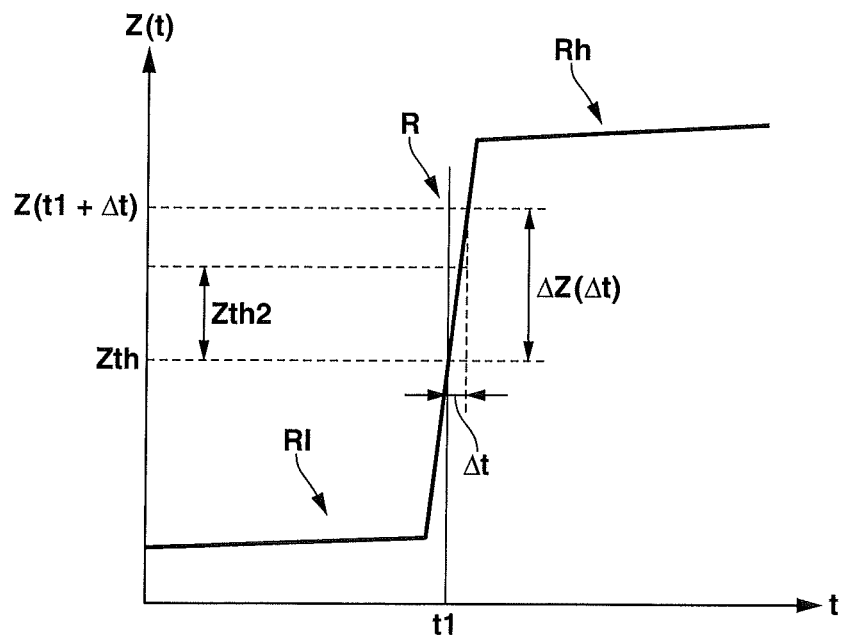
FIG. 15B is an explanatory diagram of FIG. 15A.

In an explanatory diagram of FIG. 15B, a low impedance region R1 corresponding to a region where the impedance measurement is performed and a high impedance region Rh corresponding to a region where the time measurement is performed are also schematically shown together with the impedance change region R.

When time when the impedance value Z(t) exceeds the impedance threshold Zth is represented as t1 as shown in FIG. 15B, the detecting section 39b detects whether the impedance change amount $\Delta Z(\Delta t)$ in a short time $\Delta t$ after the time changes (specifically, increases) more than the second impedance threshold Zth2.

In an example shown in FIG. 15B, the impedance change amount $\Delta Z(\Delta t)$ exceeds the second impedance threshold Zth2.

If the impedance change amount $\Delta Z(\Delta t)$ does not change exceeding the second impedance threshold Zth2, the detecting section 39b returns to the processing in step S25.

On the other hand, if the impedance change amount $\Delta Z(\Delta t)$ changes more than the second impedance threshold Zth2, the detecting section 39b detects (determines) that the impedance value Z(t) measured by the impedance measuring section 39a reaches an impedance state corresponding to a state in which moisture in the living tissue starts to evaporate. The detecting section 39b proceeds to the next step S32.

In this case, for example, the detecting section 39b of the CPU 39 has a function of a temporal impedance change amount detecting section or determining section that detects or determines a temporal impedance change amount with respect to the impedance value Z(t) measured by the impedance measuring section 39a.

A value of the second impedance threshold Zth2 can be set to correspond to the characteristic that the impedance value Zl(t) of the living tissue suddenly increases in a short time. For example, the second impedance threshold Zth2 may be set to a value equal to or larger than 100Ω. A value of the short time $\Delta t$ can be set appropriately according to the second impedance threshold Zth2.

If the detection is performed as shown in FIG. 15A, the state in which moisture in the living tissue starts to evaporate can be more surely detected by reducing the influence of noise or the like. FIG. 15A is an explanation in the case of application to FIG. 14. However, the processing can be applied to the cases of FIGS. 6, 7B, and 13 in the same manner.

The treatment of coagulation by the high-frequency current explained in the first embodiment may be performed using the probe 4C explained in the second embodiment.

Memories or the like respectively having stored therein information concerning sheath lengths, sizes of the grasping surfaces, and the like of the probes 4 and 4C may be provided in the probes 4 and 4C. The high-frequency power supply device 2 connected to the probes 4 and 4C may be able to read out the information stored in the memories and automatically set standard values of the specific times ts and ts2 and the like according to the information.

In the first or second embodiment or the like explained above, the detecting section 39b of the CPU 39 detects that the impedance value Z(t) measured by the impedance measuring section 39a reaches the impedance threshold Zth at the time when moisture in the living tissue starts to evaporate.

The impedance threshold Zth in this case is explained as being set with respect to the impedance value Z(t) measured by the impedance measuring section 39a, i.e., the combined impedance value (including the stray capacitance and the living tissue). However, the impedance threshold Zth may be modified to be set with respect to the tissue impedance Zl(t) of the living tissue as explained below.

Before treatment, an impedance value measured by the impedance measuring section 39a in a state in which a living tissue is not grasped is set as an impedance value Zab by a stray capacitance. For example, the impedance measuring section 39a calculates the tissue impedance Zl(t) of the living tissue obtained by excluding the impedance value Zab from the impedance value Z(t) measured by the impedance measuring section 39a while the living tissue is actually grasped (i.e., a combined impedance value).

The impedance threshold Zth at the time when moisture in the living tissue starts to evaporate may be set with respect to the tissue impedance Zl(t). Consequently, it is possible to perform impedance measurement more closely corresponding to the living tissue.

Different embodiments may be formed by partially combining the embodiments and the modifications explained above.

What is claimed is:
1. A high-frequency operation apparatus comprising:
a grasping portion configured to grasp a treatment target living tissue;
an electrode provided in the grasping portion configured to supply a high-frequency current to the living tissue;

a high-frequency current supplying section configured to generate the high-frequency current necessary for treatment of the living tissue via the electrode;
a high-frequency current transmitting member configured to transmit the high-frequency current generated by the high-frequency current supplying section to the electrode;
an impedance measuring section configured to measure an impedance value of the living tissue;
a detecting section configured to detect whether the impedance value measured by the impedance measuring section reaches an impedance threshold at a time when moisture in the living tissue starts to evaporate;
a calculating section configured to calculate output time in which the high-frequency current is outputted, on the basis of a length of the high-frequency current transmitting member and an area of the electrode;
a storing section configured to store the output time calculated by the calculating section;
a time measuring section configured to measure time in which the high-frequency current has been outputted at least after the detecting section detected that the impedance value of the living tissue reached the impedance threshold; and
an output control section configured to determine whether the time in which the high-frequency current has been outputted, which is measured by the time measuring section, reaches the output time stored in the storing section and to transmit, when it is determined that the time reaches the output time, an output stop signal for the high-frequency current to the high-frequency current supplying section;
wherein the detecting section determines that the impedance value measured by the impedance measuring section reaches the impedance threshold only when the impedance value reaches an impedance value several times as large as an initial impedance value of the living tissue measured by the impedance measuring section at a time of a start of supply of the high-frequency current; and
wherein the impedance value measured by the impedance measuring section is a combined impedance value obtained by combining impedance by a stray capacitance of the high-frequency current transmitting member and impedance by the living tissue connected in parallel to the impedance by the stray capacitance of the high-frequency current transmitting member.

2. The high-frequency operation apparatus according to claim 1, wherein
the time measuring section further measures, as a detection time, time from a time of a start of supply of the high-frequency current to the living tissue until the detecting section detects that the impedance value of the living tissue reaches the impedance threshold, and
the high-frequency operation apparatus further comprises a correcting section that corrects the output time based on the detection time measured by the time measuring section.

3. The high-frequency operation apparatus according to claim 2, wherein the correcting section calculates a correction coefficient according to the detection time and a standard time from the time of the start of supply of the high-frequency current until the detecting section detects that the impedance value of the living tissue reaches the impedance threshold, the standard time being stored in advance, and corrects the output time based on the calculated correction coefficient.

4. The high-frequency operation apparatus according to claim 1, wherein the detecting section detects the impedance threshold set in an impedance change region that suddenly increases stepwise in a short time from an initial impedance value measured by the impedance measuring section when the high-frequency current starts to be supplied to the living tissue to an impedance value about several times as large as the initial impedance value.

5. The high-frequency operation apparatus according to claim 1, wherein the detecting section detects that the impedance value reaches the impedance threshold at the time when moisture in the living tissue starts to evaporate only when the detecting section detects that the impedance value measured by the impedance measuring section reaches the impedance threshold and a change amount of the impedance value measured by the impedance measuring section in a short time exceeds a second impedance threshold.

6. The high-frequency operation apparatus according to claim 1, wherein the impedance threshold is set to a predetermined value within a range of $100\Omega$ to $500\Omega$, and the set predetermined value is stored in advance.

7. The high-frequency operation apparatus according to claim 1, wherein the output time is set to a predetermined value in a range of 100 ms to 20000 ms.

8. The high-frequency operation apparatus according to claim 1, wherein the storing section stores the output time set based on the length of the high-frequency current transmitting member and the area of the electrode in order to complete treatment of coagulation.

* * * * *